US006312902B1

(12) United States Patent
Shultz et al.

(10) Patent No.: US 6,312,902 B1
(45) Date of Patent: *Nov. 6, 2001

(54) NUCLEIC ACID DETECTION

(75) Inventors: John William Shultz, Verona; Martin K. Lewis, Madison; Donna Leippe, Middleton; Michelle Mandrekar, Oregon; Daniel Kephart, Cottage Grove; Richard Byron Rhodes, Madison; Christine Ann Andrews, Cottage Grove; James Robert Hartnett; Trent Gu, both of Madison; Ryan J. Olson, Middleton, all of WI (US); Roy Welch, Palo Alto, CA (US)

(73) Assignee: Promega Corporation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/406,065

(22) Filed: Sep. 27, 1999

Related U.S. Application Data

(63) Continuation-in-part of application No. 09/358,972, filed on Jul. 21, 1999, which is a continuation-in-part of application No. 09/252,436, filed on Feb. 18, 1999, which is a continuation-in-part of application No. 09/042,287, filed on Mar. 13, 1998.

(51) Int. Cl.[7] .............................. C12Q 1/68; C12P 19/34; G01N 24/00; C07H 19/04
(52) U.S. Cl. .............................. 435/6; 435/7; 435/91.2; 435/91.5; 436/173; 436/501; 536/26; 536/27; 536/28; 935/77; 935/82
(58) Field of Search ........................... 435/6, 91.2, 91.5, 435/7; 436/173, 501; 536/26, 27, 28; 935/77, 82

(56) References Cited

U.S. PATENT DOCUMENTS

| | | | |
|---|---|---|---|
| 4,303,752 | 12/1981 | Kolehmainen et al. ............... | 435/8 |
| 4,331,762 | 5/1982 | Nakajima et al. ................... | 435/190 |
| 4,338,395 | 7/1982 | Leon et al. ............................ | 435/17 |
| 4,352,881 | 10/1982 | Inagawa et al. ..................... | 435/17 |
| 4,357,420 | 11/1982 | Bostick et al. ....................... | 435/8 |
| 4,368,261 | 1/1983 | Klose et al. .......................... | 435/15 |
| 4,371,611 | 2/1983 | Fusee .................................... | 435/14 |
| 4,394,445 | 7/1983 | Nix et al. .............................. | 435/19 |
| 4,415,655 | 11/1983 | De Castro et al. .................. | 435/17 |
| 4,438,124 | 3/1984 | Melster et al. ....................... | 424/270 |
| 4,443,594 | 4/1984 | Buckmann ............................ | 536/27 |
| 4,446,231 | 5/1984 | Self ....................................... | 435/7 |
| 4,460,684 | 7/1984 | Bauer ................................... | 435/14 |
| 4,485,177 | 11/1984 | Siedel et al. ......................... | 436/547 |
| 4,595,655 | 6/1986 | Self ....................................... | 435/7 |
| 4,683,195 | 7/1987 | Mullis et al. ......................... | 435/6 |
| 4,683,202 | 7/1987 | Mullis et al. ......................... | 435/91 |
| 4,735,897 * | 4/1988 | Vary et al. ............................ | 435/6 |
| 4,743,561 | 5/1988 | Shaffar ................................. | 436/501 |
| 4,755,458 | 7/1988 | Rabbani et al. ...................... | 435/5 |
| 4,800,159 | 1/1989 | Mullis et al. ......................... | 435/172.3 |
| 5,356,776 | 10/1994 | Kambara et al. .................... | 435/6 |
| 5,389,512 | 2/1995 | Sninsky et la. ...................... | 435/5 |
| 5,391,480 | 2/1995 | Davis et al. .......................... | 435/6 |
| 5,399,491 | 3/1995 | Kacian et al. ........................ | 435/6 |
| 5,403,711 | 4/1995 | Walder et al. ........................ | 435/6 |
| 5,445,933 | 8/1995 | Eadie et al. .......................... | 435/6 |
| 5,494,810 | 2/1996 | Barany et al. ....................... | 435/91.52 |
| 5,498,523 | 3/1996 | Tabor et al. .......................... | 435/6 |
| 5,512,439 | 4/1996 | Hornes et al. ........................ | 435/6 |
| 5,516,663 | 5/1996 | Backman et al. .................... | 435/91.2 |
| 5,530,192 | 6/1996 | Murase et al. ....................... | 800/205 |
| 5,541,311 | 7/1996 | Dahlberg et al. .................... | 536/23.7 |

(List continued on next page.)

FOREIGN PATENT DOCUMENTS

| | | | |
|---|---|---|---|
| 0 229 601 | 11/1986 | (EP) . | |
| 639 647 | 7/1994 | (EP) . | |
| 0 663 447 | 12/1994 | (EP) . | |
| 0 894 867 | 11/1997 | (EP) . | |
| 2055200 | 12/1981 | (GB) ............................ | G01N/21/76 |
| WO 90/05530 | 5/1990 | (WO) . | |
| WO 91/17264 | 11/1991 | (WO) . | |
| WO 92/13963 | 8/1992 | (WO) . | |
| WO 94/25619 | 11/1994 | (WO) . | |
| WO 95/21938 | 8/1995 | (WO) . | |
| WO 96/41014 | 12/1996 | (WO) . | |
| WO 97/41256 | 11/1997 | (WO) . | |
| WO 98/13523 | 4/1998 | (WO) ............................ | C12Q/1/68 |
| WO 98/54362 | 4/1998 | (WO) . | |
| WO 98/28440 | 7/1998 | (WO) ............................ | C12Q/1/68 |

OTHER PUBLICATIONS

Seq ID No. 1, "Blast Archaeal Gemonc Sequences at Center of Marine Biotechnology" Online, May 21, 1999, Retrieved on Aug. 7, 200 @ http://Combdna.umbi.umd.edu/bags.html.

http://Comb5–156.umbi.umd.edu/egi–bin/PfurGene-.PL?GeneID=894645&Dataset=Nayb&Geneidxt–994645, Online XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

(List continued on next page.)

Primary Examiner—Jeffrey Fredman
Assistant Examiner—Arun Chakrabarti
(74) Attorney, Agent, or Firm—Welsh & Katz, Ltd.

(57) ABSTRACT

Processes are disclosed using the depolymerization of a nucleic acid hybrid to qualitatively and quantitatively analyze for the presence of a predetermined nucleic acid. Applications of those processes include the detection of single nucleotide polymorphisms, identification of single base changes, speciation, determination of viral load, genotyping, medical marker diagnostics, and the like.

48 Claims, No Drawings

U.S. PATENT DOCUMENTS

| | | | |
|---|---|---|---|
| 5,561,044 | 10/1996 | Walker et al. | 435/6 |
| 5,573,906 | 11/1996 | Bannwarth et al. | 435/6 |
| 5,622,824 | 4/1997 | Koster et al. | 435/6 |
| 5,648,232 | 7/1997 | Squirrell | 435/34 |
| 5,660,988 | 8/1997 | Duck et al. | 435/6 |
| 5,667,964 | 9/1997 | Ho | 435/5 |
| 5,683,877 | 11/1997 | Lu-Chang et al. | 435/6 |
| 5,691,146 | 11/1997 | Mayrand | 435/6 |
| 5,723,591 | 3/1998 | Livak et al. | 536/22.1 |
| 5,731,146 | 3/1998 | Duck et al. | 435/6 |
| 5,736,365 | 4/1998 | Walker et al. | 435/91.2 |
| 5,741,635 | 4/1998 | Boss et al. | 435/4 |
| 5,759,820 | 6/1998 | Hornes et al. | 435/91.1 |
| 5,763,181 | 6/1998 | Han et al. | 435/6 |
| 5,766,849 | 6/1998 | McDonough et al. | 435/6 |
| 5,786,139 | 7/1998 | Burke et al. | 435/6 |
| 5,786,183 | 7/1998 | Ryder et al. | 435/91.2 |
| 5,814,491 | 9/1998 | Vijg et al. | 435/91.2 |
| 5,824,517 | 10/1998 | Cleuziat et al. | 435/91.2 |
| 5,834,202 | 10/1998 | Auerbach | 435/6 |
| 5,840,873 | 11/1998 | Nelson et al. | 536/24.3 |
| 5,843,660 | 12/1998 | Schumm et al. | 435/6 |
| 5,849,547 | 12/1998 | Cleuziat et al. | 435/91.21 |
| 5,853,981 | 12/1998 | Kondo et al. | 435/5 |
| 5,854,033 | 12/1998 | Lizardi | 435/91.2 |
| 5,861,242 | 1/1999 | Chee et al. | 435/5 |
| 5,863,736 | 1/1999 | Haaland | 435/6 |
| 5,866,337 | 2/1999 | Schon | 435/6 |
| 5,869,252 | 2/1999 | Bouma et al. | 435/6 |
| 5,871,902 | 2/1999 | Weininger et al. | 435/5 |
| 5,876,924 | 3/1999 | Zhang et al. | 435/5 |
| 5,876,930 | 2/1999 | Livak et al. | 435/6 |
| 5,876,978 | 3/1999 | Willey et al. | 435/91.2 |
| 5,880,473 | 3/1999 | Ginestet | 250/458.1 |
| 5,882,856 | 3/1999 | Shuber | 435/6 |
| 5,885,775 | 3/1999 | Haff et al. | 435/6 |
| 5,888,819 | 3/1999 | Goelet et al. | 435/5 |
| 5,902,722 | 5/1999 | Di Cesare et al. | 435/4 |
| 6,007,987 | 12/1999 | Cantor et al. | 435/6 |
| 6,066,483 | 5/2000 | Riggs et al. | 435/194 |

OTHER PUBLICATIONS

Kawarabayashi, et al., "Complete Sequence and Gene Organization of the Genornc of hyper–thermophilic Archacbacterium, *Pyrococcus horikoshii* OT3", *DNA Research,* 5:55–76 (1998).

A.E. Sippel, "Purification and Characterization of Adenosine Triphosphate: Ribonucleic Acid Adenyltransferase from *Escherichia coli*" *Eur. J. Biochem.* 37:31–40 (1973).

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry,* 35:16610–16620 (1996).

S. Karamohamed, M. Ronaghi and P. Nyren, "Bioluminometric Method for Real–Time Detection of Reverse Transcriptase Activity", *Biotechniques,* 24:302–306 (Feb., 1998).

B. Hove–Jensen, K. W. Harlow, C.J. King, R.L. Switzer, "Phosphoribosylpyrophosphate Synthetase of *Escherichia coli*", *J. Biol. Chem.,* 261(15):6765–6771 (1986).

P. Nyren, S. Karamohamed and M. Ronaghi, "Detection of Single–Base Changes Using a Bioluminometric Primer Extension Assay", *Anal. Biochem.,* 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.,* 242:84–89 (1996).

T.A. Rozovskaya, V.O. Rechinsky, R.S. Bibilashvili, M. Y. Karpeisky, N.B. Tarusova, R.M. Khomutov, H.B.F. Dixon, "The Mechanism of Pyrophosphorolysis of RNA by RNA Polymerase", *Biochem. J.,* 224: 645–650 (1989).

M.P. Deutscher and A. Kornberg, "Enzymatic Synthesis of Deoxyribonucleic Acid", *J. Biol. Chem.,* 244(11):3019–28 (1969).

J.D. Moyer and J.F. Henderson, "Nucleoside Triphosphate Specificity of Firefly Luciferase", *Anal. Biochem.,* 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.,* 220:219–21 (1994).

S. Tabor and C.C. Richardson, "DNA Sequence Analysis With a Modified Bacteriophage T7 DNA Polymerase", *J. Biol. Chem.,* 265(14):8322–8328 (1990).

R.S. Chittock, J.–M. Hawronsky, J. Holah and C.W. Wharton, "Kinetic Aspects of ATP Amplification Reactions", *Anal. Biochem.,* 255:120–126 (Jan. 1, 1998).

Kung, et al., "Picogram Quantitation of Total DNA Using DNA–Binding Proteins in a Silicon Sensor–Based System", *Anal. Biochem.,* 187:220–227 (1990).

Srivastavan & Modak, *J. Biol. Chem.,* 255(5):2000–2004 (1980).

Sano & Feix, *Eur. J. Biochem.,* 71:577–583 (1976).

Sabina, et al., *Science,* 223:1193–1195 (1984).

Parks & Agarwal in *The Enzymes,* vol. 9:307–333, P. Boyer Ed. (1973).

Shimofuruya & Suzuki, *Biochem. Intl.,* 26(5):853–861 (1992).

Nyren, et al., "Detection of Single–Base Changes Using a Bioluminometric Primer Extension Assay", *Anal. Biochem.,* 244:367–373 (1997).

P. Bernard et al., *Am. J. Pathol.,* 153:1055–1061 (1998).

G. Garinis et al., *J. Clin. Lab. Anal.,* 13:122–125 (1999).

Holguin, et al., *Eur. J. Clin. Microbiol. Infect. Dis.,* 18:256–259 (1999).

Boriskin, et al., *Arch. Dis. Child.,* 80:132–136 (1999).

de Vega, et al., "Primer Terminus Stabilizing at the 3'–5' exonuclease active site of _29 DNA polymerase. Involvement of two amino acid residues highly conserved in proofreading DNA polymerases", *EMBO J.,* 15(5):1182–1192 (1996).

S. Patel et al., *Biochemistry,* 30:511–525 (1991).

I. Wong et al., *Biochemistry,* 30:526–537 (1991).

S. Zinnen et al., *J. Biological Chemistry,* 269(39):24195–24202 (1994).

J. Lindquist, Dept. of Bacteriology, University of Wisconsin–Madison, http://www.bact.wisc.edu/bact102/102dil3.html undated.

J. Lindquist, Dept. of Bacteriology, University of Wisconsin–Madison, http://www.bact.wisc.edu/bact102/102dil3a.html undated.

Most Probable Number (MPN), WQA Glossary of Terms, 3rd Ed., Water Quality Association undated.

P. Nyren, B. Pettersson, and M. Uhlen. "Solid Phase DNA Minisequencing by an Enzymatic Luminometric Inorganic Pyrophosphate Detection Assay,"*Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, and C. Reynolds., "Detection of Low Levels of Nucleic Acids by Enzymatic Conversion to Substrates for Luciferase", Poster presented Jul. 25–29, 1998 at a Protein Society meeting in San Diego, California.

Heid, et al., "Real Time Quantitative PCR", *Genome Research,* 6:986–994 (1996).

Nagano, et al., "Detection of Verotoxin–Producing *Escherichia coli* O157:H7 by Multiplex Polymerase Chain Reaction", *Microbiol. Immunol.,* 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation,* 5:260–262 (1995).

Poyser et al., "Multiplex genotyping for cystic fibrosis from filter paper blood spots", *Ann. Clin. Biochem.,* 35:611–615 (1998).

Caudai, et al., "Detection of HCV and GBV–C/HGV injection by multiplex PCR in plasma samples of transfused subjects", *J. Virol Meth.,* 70: 79–83 (1998).

Songsivilai, et al., "Improved Amplification System for Detection of Hepatitis C virus Genome that Simultaneously Differentiates Viral Genotype", *Southeast Asian J. Trop. Med. Public Health,* 27(2): 237–243 (1996).

Oyofo, et al., "Detection of Enterotoxigenic *Escherichia coli,* Shigella and Campylobacter spp. by Multiplex PCR Assay", *J. Diarrhoeal Dis. Res.,* 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost,* 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1998).

P. Nyren, et al., *Anal. Biochem.,* 244:367–373 (1997).

S. Borman, "Developers of Novel DNA Sequencers Claim Major Performance Advances", *C&EN ,* pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.,* 17:2503–2516 (1989).

Wu et al., *Proc. Natl. Acad. Sci.,* USA, 86:2757–2760 (1989).

T. Nikiforov, et al., *Nucl. Acids Res.,* 22:4167–4175 (1994).

C. Wittwer, et al., *Biotechniques,* 22:130–138 (1997).

P. Holland, et al., *Proc. Natl. Acad. Sci.,* USA, 88:7276–7280 (1991).

R. Kramer, et al., *Nat. Biotechnol.,* 14:303–308 (1996).

J. Shultz, D. Leippe, K. Lewis and M. Nelson, "Non–radioactive Measurement of DNA Using Coupled Enzymatic Reactions", Presentation Mar. 16–20, 1998 at a Parenteral Drug Association meeting in San Francisco, California.

* cited by examiner

```
                         SEQUENCE LISTING

<160> NUMBER OF SEQ ID NOS: 81

<210> SEQ ID NO 1
<211> LENGTH: 22
<212> TYPE: DNA
<213> ORGANISM: Homo sapiens

<400> SEQUENCE: 1
gacaaaatac ctgtattcct cg                                             22

<210> SEQ ID NO 2
<211> LENGTH: 22
<212> TYPE: DNA
<213> ORGANISM: Homo sapiens

<400> SEQUENCE: 2
gacaaaatac ctgtattcct tg                                             22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:probe for
      Rice genome (with phosphorothioate linkages)

<400> SEQUENCE: 3
cccaacacct tacagaaatt agc                                            23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:probe for
      Rice genome

<400> SEQUENCE: 4
tctcaagaca caaataactg cag                                            23

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:probe for
      "G" allele of Rice

<400> SEQUENCE: 5
```
agaacatctg caagg                                                      15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:probe for
      "T" allele of Rice

<400> SEQUENCE: 6
agaacatctg caagt                                                      15

<210> SEQ ID NO 7
<211> LENGTH: 21
<212> TYPE: DNA
<213> ORGANISM: Cytomegalovirus

<400> SEQUENCE: 7
cactttgata ttacacccat g                                               21

<210> SEQ ID NO 8
<211> LENGTH: 21
<212> TYPE: DNA
<213> ORGANISM: Cytomegalovirus

<400> SEQUENCE: 8
cactttgata ttacacccgt g                                               21

<210> SEQ ID NO 9
<211> LENGTH: 65
<212> TYPE: DNA
<213> ORGANISM: Cytomegalovirus

<400> SEQUENCE: 9
cgttgtgcgg gttcacgtcg atgagcacgt tcatgggtgt aatatcaaag tggcatacac     60
gagct                                                                 65

<210> SEQ ID NO 10
<211> LENGTH: 65
<212> TYPE: DNA
<213> ORGANISM: Homo sapiens

<400> SEQUENCE: 10
ctaatctgta agagcagatc cctggacagg cgaggaatac agagggcagc agacatcgaa     60
gagct                                                                 65

<210> SEQ ID NO 11
<211> LENGTH: 69
<212> TYPE: DNA
<213> ORGANISM: Homo sapiens

<400> SEQUENCE: 11
agctcttcga tgtctgctgc cctctgtatt cctcgcctgt ccaggatct gctcttacag      60 attagagct                                                             69

<210> SEQ ID NO 12
<211> LENGTH: 22
<212> TYPE: DNA
<213> ORGANISM: Homo sapiens

<400> SEQUENCE: 12

-continued ctgctgccct ctgtattcct cg                          22

<210> SEQ ID NO 13
<211> LENGTH: 22
<212> TYPE: DNA
<213> ORGANISM: Homo sapiens

<400> SEQUENCE: 13
ctgctgccct ctgtattcct tg                          22

<210> SEQ ID NO 14
<211> LENGTH: 22
<212> TYPE: DNA
<213> ORGANISM: Homo sapiens

<400> SEQUENCE: 14
ctgaacatgc ctgccaaaga cg                          22

<210> SEQ ID NO 15
<211> LENGTH: 22
<212> TYPE: DNA
<213> ORGANISM: Homo sapiens

<400> SEQUENCE: 15
ctgaacatgc ctgccaaaga tg                          22

<210> SEQ ID NO 16
<211> LENGTH: 22
<212> TYPE: DNA
<213> ORGANISM: Homo sapiens

<400> SEQUENCE: 16
caggaacgta ggtcggacac gt                          22

<210> SEQ ID NO 17
<211> LENGTH: 22
<212> TYPE: DNA
<213> ORGANISM: Homo sapiens

<400> SEQUENCE: 17
caggaacgta ggtcggacac at                          22

<210> SEQ ID NO 18
<211> LENGTH: 74
<212> TYPE: DNA
<213> ORGANISM: Cytomegalovirus

<400> SEQUENCE: 18
cgcttctacc acgaatgctc gcagaccatg ctgcacgaat acgtcagaaa gaacgtggag    60
cgtctgttgg agct                                   74

<210> SEQ ID NO 19
<211> LENGTH: 74
<212> TYPE: DNA
<213> ORGANISM: Cytomegalovirus

<400> SEQUENCE: 19
ccaacagacg ctccacgttc tttctgacgt attcgtgcag catggtctgc gagcattcgt    60
ggtagaagcg agct                                   74

<210> SEQ ID NO 20
<211> LENGTH: 74

```
<212> TYPE: DNA
<213> ORGANISM: mutant Cytomegalovirus

<400> SEQUENCE: 20
cgcttctacc acgaatgctc gcagatcatg ctgcacgaat acgtcagaaa gaacgtggag    60
cgtctgttgg agct                                                      74

<210> SEQ ID NO 21
<211> LENGTH: 74
<212> TYPE: DNA
<213> ORGANISM: mutant Cytomegalovirus

<400> SEQUENCE: 21
ccaacagacg ctccacgttc tttctgacgt attcgtgcag catgatctgc gagcattcgt    60
ggtagaagcg agct                                                      74

<210> SEQ ID NO 22
<211> LENGTH: 21
<212> TYPE: DNA
<213> ORGANISM: Cytomegalovirus

<400> SEQUENCE: 22
ctaccacgaa tgctcgcaga c                                              21

<210> SEQ ID NO 23
<211> LENGTH: 21
<212> TYPE: DNA
<213> ORGANISM: Cytomegalovirus

<400> SEQUENCE: 23
ctaccacgaa tgctcgcaga t                                              21

<210> SEQ ID NO 24
<211> LENGTH: 21
<212> TYPE: DNA
<213> ORGANISM: Cytomegalovirus

<400> SEQUENCE: 24
tgacgtattc gtgcagcatg g                                              21

<210> SEQ ID NO 25
<211> LENGTH: 21
<212> TYPE: DNA
<213> ORGANISM: Cytomegalovirus

<400> SEQUENCE: 25
tgacgtattc gtgcagcatg a                                              21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:probe to
      prothrombin pcr product, with phosphorothioate linkages between
      the first five bases on the 5' end

<400> SEQUENCE: 26
atagcactgg gagcattgag gc                                             22

<210> SEQ ID NO 27
<211> LENGTH: 20
<212> TYPE: DNA
```

-continued

<210> SEQ ID NO 27
<213> ORGANISM: Homo sapiens

<400> SEQUENCE: 27
gcacagacgg ctgttctctt                                          20

<210> SEQ ID NO 28
<211> LENGTH: 13
<212> TYPE: DNA
<213> ORGANISM: Homo sapiens

<400> SEQUENCE: 28
gtgactctca gcg                                                 13

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence:match to
      mutant prothrombin; complementary to wild-type 9 from 3'

<400> SEQUENCE: 29
gtgactctca gca                                                 13

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence:match to
      wild-type prothrombin; mismatch 9 from 3'

<400> SEQUENCE: 30
gtgattctca gcg                                                 13

<210> SEQ ID NO 31
<211> LENGTH: 13
<212> TYPE: DNA
<213> ORGANISM: Homo sapiens

<400> SEQUENCE: 31
gtgattctca gca                                                 13

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:wild-type
      Rice genome

<400> SEQUENCE: 32
cccaacacct tacagaaatt agc                                      23

<210> SEQ ID NO 33
<211> LENGTH: 65
<212> TYPE: DNA
<213> ORGANISM: Cytomegalovirus

<400> SEQUENCE: 33
cgttgtgcgg gttcacgtcg atgagcacgt tcacgggtgt aatatcaaag tggcatacac    60
gagct                                                          65

<210> SEQ ID NO 34

```
<211> LENGTH: 65
<212> TYPE: DNA
<213> ORGANISM: Cytomegalovirus

<400> SEQUENCE: 34
cgtgtatgcc actttgatat tacacccgtg aacgtgctca tcgacgtcaa cccgcacaac      60
gagct                                                                  65

<210> SEQ ID NO 35
<211> LENGTH: 58
<212> TYPE: DNA
<213> ORGANISM: Artificial Sequence
<220> FEATURE:
<223> OTHER INFORMATION: Description of Artificial Sequence:probe for
      THO locus with 2 bases pair mismatch

<400> SEQUENCE: 35
cccattggcc tgttcctccc ttatttccct cattcattca ttcattcatt cattcagc        58

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence:probe to THP
      locus with A to C mutation 3 form 3' terminus

<400> SEQUENCE: 36
cccattggcc tgttcctccc ttatttccct cattcattca ttcattcatt cattcccc        58

<210> SEQ ID NO 37
<211> LENGTH: 58
<212> TYPE: DNA
<213> ORGANISM: Artificial Sequence
<220> FEATURE:
<223> OTHER INFORMATION: Description of Artificial Sequence:probe to THP
      locus with A and G mutation 3 from 3' terminus

<400> SEQUENCE: 37
cccattggcc tgttcctccc ttatttccct cattcattca ttcattcatt cattcgcc        58

<210> SEQ ID NO 38
<211> LENGTH: 58
<212> TYPE: DNA
<213> ORGANISM: Artificial Sequence
<220> FEATURE:
<223> OTHER INFORMATION: Description of Artificial Sequence:THO locus
      with 6x CATT repeat

<400> SEQUENCE: 38
ggtgaatgaa tgaatgaatg aatgaatgag ggaaataagg gaggaagagg ccaatggg        58

<210> SEQ ID NO 39
<211> LENGTH: 62
<212> TYPE: DNA
<213> ORGANISM: Artificial Sequence
<220> FEATURE:
<223> OTHER INFORMATION: Description of Artificial Sequence:THO locus
      with 7x CATT repeat

<400> SEQUENCE: 39
ggtgaatgaa tgaatgaatg aatgaatgaa tgagggaaat aagggaggaa gaggccaatg      60
gg                                                                    62

<210> SEQ ID NO 40
```

```
<211> LENGTH: 70
<212> TYPE: DNA
<213> ORGANISM: Artificial Sequence
<220> FEATURE:
<223> OTHER INFORMATION: Description of Artificial Sequence:THO locus
      with 8x CATT repeat

<400> SEQUENCE: 40
ggtaggtgaa tgaatgaatg aatgaatgaa tgaatgaatg agggaaataa gggaggaaga      60
ggccaatggg                                                            70

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:CAH reverse
      probe (CYP21 only)

<400> SEQUENCE: 41
ccagagcagg gagtagtctc                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:CAH forward
      probe

<400> SEQUENCE: 42
gcatatagag catggctgtg                                                 20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence:CAH forward
      probe (CYP21 only)

<400> SEQUENCE: 43
cctgtccttg ggagactac                                                  19

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:CAH reverse
      probe

<400> SEQUENCE: 44
cccagttcgt ggtctagc                                                   18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:CAH reverse
      probe

<400> SEQUENCE: 45
tcctcactca tccccaac                                                   18
```

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence:CAH forward
      probe

<400> SEQUENCE: 46
gaaatacgga cgtcccaagg c                                              21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:CAh reverse
      probe (CYP21 only)

<400> SEQUENCE: 47
ctttccagag cagggagtag                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:CAH forward
      probe (CYP21 only)

<400> SEQUENCE: 48
ccggacctgt ccttgggaga                                                20

<210> SEQ ID NO 49
<211> LENGTH: 40
<212> TYPE: DNA
<213> ORGANISM: Homo sapiens

<400> SEQUENCE: 49
agaagcccgg ggcaagaggc aggaggtgga ggctccggag                          40

<210> SEQ ID NO 50
<211> LENGTH: 40
<212> TYPE: DNA
<213> ORGANISM: Homo sapiens

<400> SEQUENCE: 50
agcttgtctg caggaggagc tgggggctgg agggtgggaa                          40

<210> SEQ ID NO 51
<211> LENGTH: 40
<212> TYPE: DNA
<213> ORGANISM: Homo sapiens

<400> SEQUENCE: 51
tccgaaggtg aggtaacagt tgatgctgca ggtgaggaga                          40

<210> SEQ ID NO 52
<211> LENGTH: 40
<212> TYPE: DNA
<213> ORGANISM: Homo sapiens

<400> SEQUENCE: 52
tccactgcag ccatgtgcaa gtgcccttcc aggagctgtc                          40

-continued

<210> SEQ ID NO 53
<211> LENGTH: 40
<212> TYPE: DNA
<213> ORGANISM: Homo sapiens

<400> SEQUENCE: 53
tcgtggtcta gctcctccta cagtcgctgc tgaatctggg          40

<210> SEQ ID NO 54
<211> LENGTH: 40
<212> TYPE: DNA
<213> ORGANISM: Homo sapiens

<400> SEQUENCE: 54
gctaagggca caacgggcca caggcgcagc acctcggcga          40

<210> SEQ ID NO 55
<211> LENGTH: 40
<212> TYPE: DNA
<213> ORGANISM: Homo sapiens

<400> SEQUENCE: 55
cagcttgtct gcaggaggag ttgggggctg gagggtggga          40

<210> SEQ ID NO 56
<211> LENGTH: 40
<212> TYPE: DNA
<213> ORGANISM: Homo sapiens

<400> SEQUENCE: 56
ggctaagggc acaacgggcc gcaggcgcag cacctcggcg          40

<210> SEQ ID NO 57
<211> LENGTH: 18
<212> TYPE: DNA
<213> ORGANISM: Homo sapiens

<400> SEQUENCE: 57
cggagcctcc acctcccg          18

<210> SEQ ID NO 58
<211> LENGTH: 18
<212> TYPE: DNA
<213> ORGANISM: Homo sapiens

<400> SEQUENCE: 58
caccctccag cccccagc          18

<210> SEQ ID NO 59
<211> LENGTH: 18
<212> TYPE: DNA
<213> ORGANISM: Homo sapiens

<400> SEQUENCE: 59
cggagcctcc acctcctg          18

<210> SEQ ID NO 60
<211> LENGTH: 19
<212> TYPE: DNA
<213> ORGANISM: Homo sapiens

<400> SEQUENCE: 60
cctcacctgc agcatcaac          19

<210> SEQ ID NO 61
<211> LENGTH: 18
<212> TYPE: DNA
<213> ORGANISM: Homo sapiens

<400> SEQUENCE: 61
caccctccag cccccaac                                                18

<210> SEQ ID NO 62
<211> LENGTH: 19
<212> TYPE: DNA
<213> ORGANISM: Homo sapiens

<400> SEQUENCE: 62
cctcacctgc agcatcatc                                               19

<210> SEQ ID NO 63
<211> LENGTH: 15
<212> TYPE: DNA
<213> ORGANISM: Homo sapiens

<400> SEQUENCE: 63
cctggaaggg cactt                                                   15

<210> SEQ ID NO 64
<211> LENGTH: 15
<212> TYPE: DNA
<213> ORGANISM: Homo sapiens

<400> SEQUENCE: 64
cctggaaggg cacgt                                                   15

<210> SEQ ID NO 65
<211> LENGTH: 18
<212> TYPE: DNA
<213> ORGANISM: Homo sapiens

<400> SEQUENCE: 65
gattcagcag cgactgta                                                18

<210> SEQ ID NO 66
<211> LENGTH: 18
<212> TYPE: DNA
<213> ORGANISM: Homo sapiens

<400> SEQUENCE: 66
gattcagcag cgactgca                                                18

<210> SEQ ID NO 67
<211> LENGTH: 18
<212> TYPE: DNA
<213> ORGANISM: Homo sapiens

<400> SEQUENCE: 67
cgaggtgctg cgcctgcg                                                18

<210> SEQ ID NO 68
<211> LENGTH: 18
<212> TYPE: DNA
<213> ORGANISM: Homo sapiens

<400> SEQUENCE: 68
cgaggtgctg cgcctgtg                                                18

<210> SEQ ID NO 69
<211> LENGTH: 20
<212> TYPE: DNA
<213> ORGANISM: Homo sapiens

<400> SEQUENCE: 69
gggatcacat cgtggagatg                                           20

<210> SEQ ID NO 70
<211> LENGTH: 20
<212> TYPE: DNA
<213> ORGANISM: Homo sapiens

<400> SEQUENCE: 70
gggatcacaa cgaggagaag                                           20

<210> SEQ ID NO 71
<211> LENGTH: 65
<212> TYPE: DNA
<213> ORGANISM: Cytomegalovirus

<400> SEQUENCE: 71
cgtgtatgcc actttgatat tacacccatg aacgtgctca tcgacgtcaa cccgcacaac     60
gagct                                                              65

<210> SEQ ID NO 72
<211> LENGTH: 65
<212> TYPE: DNA
<213> ORGANISM: Cytomegalovirus

<400> SEQUENCE: 72
cgttgtgcgg gttcacgtcg atgagcacgt tcatgggtgt aatatcaaag tggcatacac     60
gagct                                                              65

<210> SEQ ID NO 73
<211> LENGTH: 58
<212> TYPE: DNA
<213> ORGANISM: Artificial Sequence
<220> FEATURE:
<223> OTHER INFORMATION: Description of Artificial Sequence:probe to THO
      locus with A and G mutation 3 from 3' terminus

<400> SEQUENCE: 73
cccattggcc tgttcctccc ttatttccct cattcattca ttcattcatt cattgacc       58

<210> SEQ ID NO 74
<211> LENGTH: 58
<212> TYPE: DNA
<213> ORGANISM: Artificial Sequence
<220> FEATURE:
<223> OTHER INFORMATION: Description of Artificial Sequence:probe for
      THO locus with additional base pair mismatch 4 from 3' terminus

<400> SEQUENCE: 74
cccattggcc tgttcctccc ttatttccct cattcattca ttcattcatt cattaacc       58

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence:probe for
      NDPK from Pyrococcus furiosis

<400> SEQUENCE: 75
atnatnaaag ccngatcggc ngt          23

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence:probe for
      NDPK from Ptrococcus furiosis

<400> SEQUENCE: 76
aaagtcnccn ctgnatngtn ccngg        25

<210> SEQ ID NO 77
<211> LENGTH: 21
<212> TYPE: DNA
<213> ORGANISM: Pyrococcus furiosus

<400> SEQUENCE: 77
gagaagcact atgaggagca c            21

<210> SEQ ID NO 78
<211> LENGTH: 486
<212> TYPE: DNA
<213> ORGANISM: Pyrococcus furiosus

<400> SEQUENCE: 78
atgaacgaag ttgaaagaac attggtaatc ataaagcccg acgcagtagt tagggtcta     60
ataggtgaaa ttataagcag gtttgagaag aaaggcctca agattgttgg aatgaagatg    120
atctggatag acaggagtt ggctgagaag cactatgagg agcacaaagg aaagcccttc     180
tttgaggctc tcatagatta cataacgaaa gctccagtag ttgttatggt ggttgaggga    240
aggtatgcag tagaagtagt tagaaagatg gctggagcta ctgatccaaa ggacgcagca    300
cctgggacaa ttaggggaga ttatggactt gacataggag atgcaatcta caacgtgatt    360
catgccagtg attcaaagga aagtgcggag agggaaataa gcctgtactt taaacctgaa    420
gaaatttatg aatactgcaa agctgcagat tggttttaca gggaaaagaa gcaggctaaa    480
tgctga                                                               486

<210> SEQ ID NO 79
<211> LENGTH: 108
<212> TYPE: DNA
<213> ORGANISM: Pyrococcus furiosus

<400> SEQUENCE: 79
mnvrtvkdav vrggsrkkgk vgmkmwdrak hyhkgkadyt kavvvmvvgr yavvvrkmag     60
atdkdaagtr gdygdgdayn vhasdsksar sykyyckaad wyrkkakc                 108

<210> SEQ ID NO 80
<211> LENGTH: 25
<212> TYPE: DNA
<213> ORGANISM: Pyrococcus furiosus

<400> SEQUENCE: 80
gggtgctttt catgaacgaa gttga        25

<210> SEQ ID NO 81
<211> LENGTH: 27

-continued

<212> TYPE: DNA
<213> ORGANISM: Pyrococcus furiosus

<400> SEQUENCE: 81
aagggcaaaa attctagagt tcagcat                    27

NUCLEIC ACID DETECTION

CROSS-REFERENCE TO RELATED APPLICATIONS

This application is a continuation-in-part of U.S. Ser. No. 09/358,972, filed on Jul. 21, 1999, which is a continuation-in-part of U.S. Ser. No. 09/252,436, filed on Feb. 18, 1999, which is a continuation-in-part of U.S. Ser. No. 09/042,287, filed Mar. 13, 1998, all of which are incorporated herein by reference.

TECHNICAL FIELD

The invention relates to nucleic acid detection. More specifically, the invention relates to enhanced detection of targeted, predetermined nucleic acid sequences in nucleic acid target/probe hybrids, and the various applications of the enhanced detection.

BACKGROUND OF THE INVENTION

Methods to detect nucleic acids and to detect specific nucleic acids provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, or the ability to automate the process.

The detection of nucleic acids or specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g. tissue, sputum, urine, blood, semen, saliva) has applications in forensic science, such as the identification and exclusion of criminal suspects and paternity testing as well as medical diagnostics.

Some general methods to detect nucleic acids are not dependent upon a priori knowledge of the nucleic acid sequence. A nucleic acid detection method that is not sequence specific, but is RNA specific is described in U.S. Pat. No. 4,735,897, where RNA is depolymerized using a polynucleotide phosphorylase (PNP) in the presence of phosphate or using a ribonuclease. PNP stops depolymerizing when at or near a double-stranded RNA segment. The form of double-stranded RNA can sometimes be a type of secondary structure, as is common in ribosomal RNA, transfer RNA, viral RNA, and the message portion of mRNA. PNP depolymerization of the polyadenylated tail of mRNA in the presence of inorganic phosphate forms ADP. Alternatively, depolymerization using a ribonuclease forms AMP. The formed AMP is converted to ADP with myokinase, and ADP is converted into ATP by pyruvate kinase or creatine phosphokinase. Either the ATP or the byproduct from the organophosphate co-reactant (pyruvate or creatine) is detected as an indirect method of detecting mRNA.

In U.S. Pat. No. 4,735,897, ATP is detected by a luciferase detection system. In the presence of ATP and oxygen, luciferase catalyzes the oxidation of luciferin, producing light that can then be quantified using a luminometer. Additional products of the reaction are AMP, pyrophosphate and oxyluciferin.

Duplex DNA can be detected using intercalating dyes such as ethidium bromide. Such dyes are also used to detect hybrid formation.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Fluorescence techniques are also known for the detection of nucleic acid hybrids. U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of a nucleic acid hybrid in a 5' to 3' direction to release a fluorescent signal from proximity to a fluorescence quencher, for example, TaqMan® (Perkin Elmer; U.S. Pat. Nos. 5,691,146 and 5,876,930).

Enzymes having template-specific polymerase activity for which some 3'→5' depolymerization activity has been reported include E. coli DNA Polymerase (Deutscher and Kornberg, J. Biol. Chem., 244(11):3019–28 (1969)), T7

DNA Polymerase (Wong et al., *Biochemistry* 30:526–37 (1991); Tabor and Richardson, *J. Biol. Chem.* 265: 8322–28 (1990)), *E. coli* RNA polymerase (Rozovskaya et al., *Biochem. J.* 224:645–50 (1994)), AMV and RLV reverse transcriptases (Srivastava and Modak, *J. Biol. Chem.* 255: 2000–4 (1980)), and HIV reverse transcriptase (Zinnen et al., *J. Biol. Chem.* 269:24195–202 (1994)). A template-dependent polymerase for which 3' to 5' exonuclease activity has been reported on a mismatched end of a DNA hybrid is phage 29 DNA polymerase (de Vega, M. et al. *EMBO J.*, 15:1182–1192, 1996).

There is a need for alternative methods for detection of nucleic acid hybrids. There is a demand for highly sensitive methods that are useful for determining the presence or absence of specific nucleic acid sequences, for example methods to determine viral load that are able to reliably detect as few as 10 copies of a virus present in a body, tissue, fluid, or other biological sample. There is a great demand for such methods to determine the presence or absence of nucleic acid sequences that differ slightly from sequences that might otherwise be present. There is a great demand for methods to determine the presence or absence of sequences unique to a particular species in a sample. There is also a great demand for methods that are more highly sensitive than the known methods, quantitative, highly reproducible and automatable.

It would be beneficial if another method were available for detecting the presence of a sought-after, predetermined target nucleotide sequence or allelic or polynucleotide variant. It would also be beneficial if such a method were operable using a sample size of the microgram to picogram scale. The disclosure that follows provides one such method.

BRIEF SUMMARY OF THE INVENTION

A method of this invention is used to determine the presence or absence of a predetermined (known) nucleic acid target sequence in a nucleic acid sample. Such a method utilizes an enzyme that can depolymerize the 3'-terminus of an oligonucleotide probe hybridized to a nucleic acid target sequence to release one or more identifier nucleotides whose presence can then be determined.

In one aspect of a process of the invention, the depolymerizing enzyme (enzymes are further identified herein), whose activity is to release nucleotides, is a template-dependent polymerase, whose activity is to depolymerize hybridized nucleic acid whose 3'-terminal nucleotide is matched, in the 3' to 5' direction in the presence of pyrophosphate ions to release one or more nucleotides. Thus, the enzyme's activity is to depolymerize hybridized nucleic acid to release nucleotides under depolymerizing conditions. Preferably, this enzyme depolymerizes hybridized nucleic acids whose bases in the 3'-terminal region of the probe are matched with total complementarity to the corresponding bases of the nucleic acid target.

In an alternative aspect of the process, the depolymerizing enzyme, whose activity is to release nucleotides, exhibits a 3' to 5' depolymerizing activity in which hybridized nucleic acids having one or more mismatched bases at the 3'-terminus of the hybridized probe are depolymerized. Thus, the enzyme's activity is to depolymerize hybridized nucleic acid to release identifier nucleotides under depolymerizing conditions. In this embodiment, the hybrid can be separated from the free probe prior to enzyme treatment. In some embodiments, an excess of target can be used so that the concentration of free probe in the enzyme reaction is extremely low.

In still another alternative aspect of a process of the invention, the depolymerizing enzyme exhibits a 3' to 5' exonuclease activity on a double-stranded DNA substrate having one or more matched bases at the 3' terminus of the hybrid. The enzyme's activity is to depolymerize hybridized nucleic acid to release nucleotides containing a 5' phosphate under depolymerizing conditions.

In particularly preferred embodiments, ATP molecules are formed by a phosphate transferring step, (e.g. using NDPK in the presence of ADP), from the dNTPs produced by the depolymerizing step. In some embodiments where greater sensitivity is desired, the ATP can be amplified to form a plurality of ATP molecules.

One embodiment of the invention contemplates a method for enhancing the discrimination of analytical output between a target/probe hybrid with a matched base at an interrogation position and a substantially identical target/probe hybrid with a mismatched base at the same interrogation position. This embodiment is useful for the determination of the presence or absence of a predetermined nucleic acid in a target nucleic acid sequence in a nucleic acid sample, and comprises the following steps.

A plurality of separate treated samples is provided. Each treated sample contains a nucleic acid target sequence that may contain the predetermined nucleic acid. Each nucleic acid target sequence is hybridized with a nucleic acid probe.

A first probe of a first treated sample comprises a 3'-terminal region sequence that is complementary to the nucleic acid target sequence. The first probe includes an identifier nucleotide. This identifier nucleotide is complementary to the first-named target nucleic acid. The first probe also contains a second sequence otherwise complementary to the nucleic acid target sequence except for a second predetermined nucleotide that is not complementary to the target sequence and is located about 2 to about 10 nucleotides upstream from the 3'-terminal nucleotide of the first probe. This second predetermined nucleotide mismatched base acts to further destabilize the hybridized probe and enhances discrimination as discussed above.

A second probe of a second treated sample contains a 3'-terminal region sequence that is complementary to the same nucleic acid target sequence as the first probe, except for an identifier nucleotide in the 3'-terminal region that is not complementary to the first predetermined nucleic acid of the first-named target nucleic acid. The second probe also contains a second sequence otherwise complementary to the target sequence except for a second predetermined nucleotide (the same second predetermined nucleotide as the first probe) that is not complementary to the target sequence and is present about 2 to about 10 nucleotides upstream from the 3'-terminal nucleotide of said probe.

Each treated sample is admixed with a depolymerizing amount of an enzyme whose activity is to release one or more nucleotides from the 3'-terminus of a hybridized nucleic acid probe to form a treated reaction mixture. The treated reaction mixtures are maintained for a time period sufficient to permit the enzyme to depolymerize a hybridized nucleic acid probe and release an identifier nucleotide therefrom.

The samples are analyzed for the presence or absence of released identifier nucleotide to obtain an analytical output. Analysis can include utilization of released identifier nucleotide to form ATP by NDPK in the presence of ADP, followed by analysis of the amount of ATP present. Analysis may also be performed by alternative means including mass spectrometry and fluorescence spectroscopy, further described herein.

The ratio of the analytical output from the sample containing the first probe relative to that of the sample containing the second probe is enhanced compared to the ratio of the analytical output from a similar set of treated samples (samples 3 and 4) that contain the same target and probes as do samples 1 and 2 respectively, but whose probes do not contain the second predetermined nucleic acid that is not complementary [destabilizing mismatched base(s)] when hybridized with the target. This second predetermined nucleic acid in the first and second probes is located at about 2 to about 10 nucleotides upstream from the 3' terminal nucleotide of the probe, preferably 3 to 6 nucleotides upstream. Therefore, the third probe is identical to the first probe except that the third probe does not contain a nucleotide, located at about 2 to about 10 nucleotides upstream from the 3' terminal nucleotide, that is a mismatch when the probe is hybridized to the target sequence. Likewise, the fourth probe is identical to the second probe except that the fourth probe does not contain a nucleotide, located at about 2 to about 10 nucleotides upstream from the 3' terminal nucleotide that is a mismatch when the probe is hybridized to the target sequence. Instead, the third and fourth probes have a complementary base at the same position as the second predetermined nucleic acid that is not complementary in the first and second probes. The nucleic acid target sequence is substantially the same for all four probes.

A method for decreasing background signal in an assay to detect the presence or absence of predetermined nucleic acid target sequence in a nucleic acid sample is also contemplated. That method comprises the steps of:

A sample to be assayed is admixed with a pair of amplifying primers to form an extension composition in which the amplifying primers are hybridized to the nucleic acid target sequence when the target sequence is present. The amplifying primers contain a 5'-terminus with a plurality of terminal bases resistant to cleavage by 5' to 3' T7 gene 6 exonuclease or 5' to 3' T3 gene exonuclease 6 or λ exonuclease. The extension composition is reacted with a polymerase and nucleotides to extend the amplifying primers to form nucleic acid strands when the predetermined nucleic acid target sequence is present in the extension composition and form a treated extension composition. The treated extension composition is admixed with T7 gene 6 exonuclease or T3 gene 6 exonuclease or λ exonuclease to form a strand removal composition. The strand removal composition is maintained for a time period sufficient to substantially degrade hybridized nucleic acid strands that are not resistant to cleavage by T7 gene 6 exonuclease or T3 gene 6 exonuclease or λ exonuclease to form a treated sample.

The treated sample is admixed with a nucleic acid probe that hybridizes with the extended amplifying primer and includes an identifier nucleotide in the 3'-terminal region to form second hybrids. The second hybrids are admixed with a depolymerizing amount of an enzyme whose activity is to release one or more nucleotides from the 3'-terminus of a hybridized nucleic acid probe to form a first treated reaction mixture. The treated reaction mixture is maintained for a time period sufficient to permit the enzyme to depolymerize hybridized nucleic acid and release identifier nucleotides therefrom. The presence of released identifier nucleotides is assayed (analyzed) to obtain an analytical output, the analytical output indicating the presence or absence of said nucleic acid target sequence.

Preferably, the 5'-terminus of the amplifying primer contains two or three exonuclease-resistant bonds. More preferably, two or more exonuclease-resistant phosphorothioate linkages are present at the 5'-terminus of a primer. Most preferably, two or three phosphorothioate linkages are so present. It is also contemplated that a plurality of different primer pairs be admixed with a sample to be assayed, the primers being hybridized to a plurality of different target nucleic acid sequences when those target sequences are present in the sample.

A further embodiment of the invention contemplates a process to determine the presence or absence of a predetermined single-stranded nucleic acid target sequence. Such a process comprises the following steps.

A depolymerization reaction mixture is provided that comprises a pair of first and second nucleic acid probes and a hybrid between a third probe and the nucleic acid target sequence. The first and second nucleic acid probes are complementary and form 3'-overhangs on both ends of the duplex formed when each of the pair of complementary nucleic acid probes is hybridized with the other. The first of those probes is complementary to the nucleic acid target sequence, whereas the second has the sequence of the nucleic acid target. A hybrid between a third probe and the nucleic acid target sequence is present in the depolymerization reaction mixture when the nucleic acid target sequence is present in the nucleic acid sample. Each of the first and third probes has an identifier nucleotide in its 3'-terminal region. The reaction mixture further comprises a depolymerizing amount of an enzyme whose activity is to release nucleotides from the 3'-terminus of a hybridized nucleic acid.

The reaction mixture is maintained under depolymerization conditions for a time period sufficient to permit the enzyme to depolymerize the 3'-terminal region of the hybridized third probe to release identifier nucleotides and form a first treated reaction mixture.

The products of the first treated reaction mixture are denatured to form a denatured treated reaction mixture.

The denatured treated reaction mixture is maintained under hybridizing conditions for a time period sufficient to form a second depolymerization reaction mixture. That second depolymerization reaction mixture comprises two components. The first is a hybrid formed between the first probe and the nucleic acid target sequence, when the nucleic acid target sequence is present in the nucleic acid sample. The second component is a hybrid formed between the 3'-terminal-depolymerized third probe and the second nucleic acid probe. One end of that second hybrid has a blunt end or a 5'-overhang, as well as an identifier nucleotide in the 3'-terminal region.

The first and second hybrid components of the second reaction mixture are depolymerized to release identifier nucleotide from the 3'-terminal regions of the hybrids to form a second treated reaction mixture. The second treated reaction mixture is analyzed for the presence of released identifier nucleotide to obtain an analytical output, the analytical output indicating the presence or absence of said nucleic acid target sequence.

In preferred practice, the first and third probes are the same. In addition, the denaturation, annealing and depolymerization steps are preferably repeated to further increase the number of nucleic acid hybrids from which identifier nucleotides are released prior to analysis of the amplification reaction mixture to detect released identifier nucleotide. Most preferably, the depolymerizing enzyme is thermostable.

A related embodiment of the invention contemplates a process to determine the presence or absence of a predetermined double-stranded nucleic acid target sequence in a sample. The process comprises the following steps.

A first reaction mixture comprises first and second nucleic acid probes, third and fourth nucleic acid probes, and a depolymerizing enzyme. The first and second complementary nucleic acid probes form 3'-overhangs on both ends of the duplex formed when each of the complementary nucleic acid probes is hybridized with the other. Each of those probes is complementary to one or the other strand of the nucleic acid target sequence and has an identifier nucleotide in its 3'-terminal region. Hybrids between a third and fourth probe and each of the two strands of the nucleic acid target sequence are present when the nucleic acid target sequence is present in the nucleic acid sample. The third and fourth probes each have an identifier nucleotide in its 3'-terminal region. Also present is a depolymerizing amount of a depolymerizing enzyme whose activity is to release nucleotides from the 3'-terminus of a hybridized nucleic acid.

The first reaction mixture is maintained for a time period sufficient to permit the enzyme to depolymerize hybridized nucleic acid to release identifier nucleotide from the 3'-terminal region of the hybridized third and fourth probes and form a treated first reaction mixture. The products of the treated first reaction mixture are denatured to form a denatured treated reaction mixture.

The denatured treated reaction mixture is maintained under hybridizing conditions for a time period sufficient to form a second reaction mixture. That second reaction mixture comprises two components. A first component is comprised of hybrids that lack a 3'-overhang between each of the strands of the target nucleic acid and each of the first and second probes, when the nucleic acid target sequence is present in the nucleic acid sample. A second component is comprised of hybrids between each of the first and second probes and 3'-terminal region-depolymerized third and fourth probes. Each of the hybrids of each of the components contains one end that is blunt or has a 5'-overhang, as well as an identifier nucleotide in the 3'-terminal region.

The hybrids of the first and second components above are depolymerized to release identifier nucleotide from the 3'-terminus of the hybridized probes to form a second treated reaction mixture. The second treated reaction mixture is analyzed for the presence of released identifier nucleotide to obtain an analytical output, the analytical output indicating the presence or absence of said nucleic acid target sequence.

In preferred practice, the first and third probes are the same. In addition, the denaturation, annealing and depolymerization steps are preferably repeated to further increase the number of nucleic acid hybrids from which identifier nucleotides are released prior to analysis of the amplification reaction mixture to detect released identifier nucleotide.

It is contemplated that an analytical output of the methods of the invention can be obtained in a variety of ways. The analytical output can be ascertained by luminescence spectroscopy. In some preferred embodiments, analysis for released 3'-terminal region indicator nucleotides comprises the detection of ATP, either by a luciferase detection system (luminescence spectroscopy) or an NADH detection system (fluorescence spectroscopy). In particularly preferred embodiments, ATP molecules are formed by a phosphate transferring step, for example using an enzyme such as NDPK in the presence of ADP, from the nucleotide triphosphates produced by the depolymerizing step. In some embodiments where greater sensitivity is desired, the ATP is amplified to form a plurality of ATP molecules. In the ATP detection embodiments, typically the enzyme (NDPK) for converting nucleotides and added ADP into ATP is present in the depolymerization reaction, and thus they are denoted as a "one pot" method.

In an alternative embodiment, the analytical output is obtained by fluorescence spectroscopy. Use of a wide variety of fluorescence detection methods is contemplated. In one exemplary contemplated method, an identifier nucleotide includes a fluorescent label. An identifier nucleotide can be fluorescently labeled prior to, or after, release of the identifier nucleotide. It is also contemplated that other than a released identifier nucleotide contains a fluorescent tag. In such an embodiment, the release of nucleotides in a process of the invention is ascertained by a determination of a difference in the length of the polynucleotide probe, for example by capillary electrophoresis imaged by a fluorescent tag at the 5' terminus of the probe or in a region other than the 3' terminal region.

In an alternative embodiment the analytical output is obtained by mass spectrometry. It is preferred here that an identifier nucleotide be a nucleotide analog or a labeled nucleotide and have a molecular mass that is different from the mass of a usual form of that nucleotide, although a difference in mass is not required. It is also noted that with a fluorescently labeled identifier nucleotide, the analytical output can also be obtained by mass spectrometry. It is also contemplated that the analysis of released nucleotide be conducted by ascertaining the difference in mass of the probe after a depolymerization step of a process of the invention.

In another alternative embodiment, the analytical output is obtained by absorbance spectroscopy. Such analysis monitors the absorbance of light in the ultraviolet and visible regions of the spectrum to determine the presence of absorbing species. In one aspect of such a process, released nucleotides are separated from hybridized nucleic acid and other polynucleotides by chromatography (e.g. HPLC or GC) or electrophoresis (e.g. PAGE or capillary electrophoresis). Either the released identifier nucleotide or the remainder of the probe can be analyzed for to ascertain the release of the identifier nucleotide in a process of the invention. In another aspect of such a process a label may be incorporated in the analyzed nucleic acid.

Where the identifier nucleotide in the above methods of the invention is a nucleoside triphosphate, in preferred embodiments, the nucleoside triphosphate is used to convert ADP to ATP using the enzyme NDPK. Preferably, the NDPK enzyme is encoded by *Pyrococcus furiosis*.

In preferred embodiments of the methods of the invention, the enzyme whose activity is to release one or more nucleotides from the 3'-terminus of a hybridized nucleic acid probe is selected from the group consisting of the The triple mutant DNA polymerase, Bst DNA polymerase, Ath DNA polymerase, Taq DNA polymerase and Tvu DNA polymerase.

The present invention has many benefits and advantages, several of which are listed below.

One benefit of the invention is that, in some embodiments, nucleic acid hybrids can be detected with very high levels of sensitivity without the need for radiochemicals or electrophoresis.

An advantage of the invention is that the presence or absence of one or more target nucleic acid(s) can be detected reliably, reproducibly, and with great sensitivity.

A further benefit of the invention is that quantitative information can be obtained about the amount of a target nucleic acid sequence in a sample.

A further advantage of the invention is that very slight differences in nucleic acid sequence are detectable, including single nucleotide polymorphisms (SNPs).

Yet another benefit of the invention is that the presence or absence of a number of target nucleic acid sequences can be determined in the same assay.

Yet another advantage of the invention is that the presence or absence of a target nucleic acid can be determined with a small number of reagents and manipulations.

Another benefit of the invention is that the processes lend themselves to automation.

Still another benefit of the invention is its flexibility of use in many different types of applications and assays including, but not limited to, detection of mutations, translocations, and SNPs in nucleic acid (including those associated with genetic disease), determination of viral load, species identification, sample contamination, and analysis of forensic samples.

Still further benefits and advantages of the invention will become apparent from the specification and claims that follow.

DEFINITIONS

To facilitate understanding of the invention, a number of terms are defined below.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "TP" stands for triphosphate, "DP" stands for diphosphate, and "MP" stands for monophosphate, in conformity with standard usage in the art. Subgeneric designations for ribonucleotides are "NMP", "NDP" or "NTP", and subgeneric designations for deoxyribonucleotides are "dNMP", "dNDP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "wild-type", as used herein, refers to a gene or gene product that has the characteristics of that gene or gene product that is most frequently observed in a population and is thus arbitrarily designated the "normal" or "wild-type" form of the gene. In contrast, the term "modified" or "mutant" as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to site within a nucleic acid where one or more bases are mutated by deletion or insertion, so that the nucleic acid sequence differs from the wild-type sequence.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position."

DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'-ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to a nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". Herein, oligonucleotides or polynucleotides may contain a phosphorothioate bond.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "$T_m$" is used in reference to the "melting temperature". The melting temperature is the temperature at which 50% of a population of double-stranded nucleic acid molecules becomes dissociated into single strands. Equations for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: $T_m$=[(number of A+T)×2° C.+(number of G+C)×4° C.]. C. R. Newton et al. *PCR*, $2^{nd}$ Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

The term "interrogation position", as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide", as used herein, refers to a nucleotide whose presence is to be detected in a process of the invention to identify that a depolymerization reaction has occurred. The particular application of a method of the invention affects which residues are considered an identifier nucleotide. For a method using ATP detection (e.g. luciferase/luciferin or NADH) wherein, during analysis, all nucleotides released in the depolymerization are used to create ATP with an enzyme such as NDPK, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide may be labeled prior to or after release from the nucleic acid. For radiographic detection, a radioactively-labeled nucleotide is an identifier nucleotide. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

The term "sample", as used herein, is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection", as used herein, refers to quantitatively or qualitatively identifying a nucleotide or nucleic acid within a sample.

The term "depolymerization", as used herein, refers to the removal of a nucleotide from the 3' end of a nucleic acid.

The term "allele", as used herein, refers to an alternative form of a gene and the term "locus", as used herein, refers to a particular place on a nucleic acid molecule.

DETAILED DESCRIPTION OF THE INVENTION

A method of this invention is used to determine the presence or absence of at least one predetermined (known) nucleic acid target sequence in a nucleic acid sample. A nucleic acid target is "predetermined" in that its sequence must be known to design a probe that hybridizes with that target. However, it should be noted that a nucleic acid target sequence, as used with respect to a process of this invention, may merely act as a reporter to signal the presence of a different nucleic acid whose presence is desired to be determined. That other nucleic acid of interest does not have to have a predetermined sequence. Furthermore, a process of the invention is useful in determining the identity of base within a target where only enough of the sequence is known to design a probe that hybridizes to that target with partial complementarity at the 3'-terminal region of the probe.

Such a method utilizes an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

A nucleic acid target sequence is predetermined in that a nucleic acid probe is provided to be partially or totally complementary to that nucleic acid target sequence. A nucleic acid target sequence is a portion of nucleic acid sample with which the probe hybridizes if that target sequence is present in the sample.

A first step of the method is admixing a sample to be assayed with one or more nucleic acid probes. The admixing of the first step is typically carried out under low stringency hybridizing conditions to form a hybridization composition. In such a hybridization composition, the 3'-terminal region of the nucleic acid probe(s) (i) hybridizes with partial or total complementarity to a nucleic acid target sequence that may be present in the sample; and (ii) includes an identifier nucleotide in the 3'-terminal region.

Preferably, the nucleic acid probe is designed to not hybridize with itself to form a hairpin structure in such a way as to interfere with hybridization of the 3'-terminal region of the probe to the target nucleic acid. Parameters guiding probe design are well known in the art.

The hybridization composition is maintained under hybridizing conditions for a time period sufficient to form a treated sample that may contain at least one predetermined nucleic acid target sequence hybridized with a nucleic acid probe.

In the event that the sample to be assayed does not contain a target sequence to which the probe hybridizes, no hybridization takes place. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

The treated sample is admixed with a depolymerizing amount of an enzyme whose activity is to release one or more identifier nucleotides from the 3'-terminal region of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzyme reaction conditions is discussed in detail hereinafter.

The depolymerization reaction mixture is maintained under depolymerizing conditions for a time period sufficient to permit the enzyme to depolymerize hybridized nucleic acid and release identifier nucleotides therefrom to form a treated reaction mixture.

The presence or absence of released identifier nucleotides is then determined to obtain an analytical output. The analytical output indicates the presence or absence of at least the one nucleic acid target sequence.

Processes of the invention can also be concerned with the degree of hybridization of the target to the 3'-terminal region of the probe. Examples hereinafter show that the distinction between a matched and mismatched base becomes less notable as a single mismatch is at a position further upstream from the 3'-terminal region position. There is very little discrimination between a match and mismatch when a single mismatch is ten to twelve residues from the 3'-terminal nucleotide position, whereas great discrimination is observed when a single mismatch is at the 3'-terminus. Therefore, when the degree of complementarity (partial or total complementarity) of a nucleic acid probe hybridized to a target nucleic acid sequence is referred to herein in regard to an identifier nucleotide, this is to be understood to be referring to within the 3'-terminal region, up to about ten residues of the 3'-terminal position.

In particular embodiments of the invention, it is desirable to include a destabilizing mismatch in or near the 3'-terminal region of the probe. In an example of such an embodiment, the goal is to determine whether a nucleotide at an interrogation position is a match or a mismatch with the target. Better discrimination between match and mismatch at the interrogation position is observed when an intentional mismatch is introduced about 2 to about 10 nucleotides from the interrogation position or preferably about 2 to about 6 nucleotides from the interrogation position.

The distinction of the analytical output between matched and mismatched nucleotides when there is more than a single base that is mismatched within the 3'-terminal region can be evident even if mismatches are beyond position 10 from the terminus, for example at position 11 and 12 upstream of the 3'-terminal nucleotide. Thus, the phrases "about 10" and "3'-terminal region" are used above. The 3'-terminal region therefore comprises the approximately 10 residues from the 3'-terminal nucleotide (or 3' terminus) position of a nucleic acid.

Hybridization conditions can be empirically ascertained for a control sample for various time periods, pH values, temperatures, nucleic acid probe/target combinations and the like. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

The conditions and considerations with respect to hybridization of PCR primers to template nucleic acid in PCR are applicable to the hybridization of nucleic acid probes to target sequences in a process of the invention. Such hybridization conditions are well known in the art, and are a matter of routine experimentation depending on factors including the sequence of the nucleic acid probe and the target nucleic acid [sequence identity (homology), length and G+C content] molar amounts of nucleic acid present, buffer, salt content and duplex $T_m$ among other variables.

Processes of the invention are sensitive and hybridization conditions of low stringency (e.g. temperature of 0–4° C.) are sufficient, but moderate stringency conditions (i.e. temperatures of 40–60° C.) also permit hybridization and provide acceptable results. This is true for all processes of the invention.

In one contemplated embodiment of the invention, the enzyme whose activity is to depolymerize hybridized nucleic acid to release nucleotides from the probe 3'-terminal end is a template-dependent polymerase. In such an embodiment, the reverse of a polymerase reaction is used to depolymerize a nucleic acid probe, and the identifier nucleotide is released when the 3'-terminal nucleotide of the nucleic acid probe hybridizes with total complementarity to its nucleic acid target sequence. A signal confirms the presence of a nucleic acid target sequence that has the sequence sufficiently complementary to the nucleic acid probe to be detected by the process of the invention.

In an embodiment that uses a 3'→5' exonuclease activity of a polymerase, such as Klenow or T4 DNA polymerase (but not limited to those two enzymes), to depolymerize a nucleic acid probe, an identifier nucleotide is released when the 3'-terminal residue of the nucleic acid probe is mismatched and therefore there is only partial complementarity of the 3'-terminus of the nucleic acid probe to its nucleic acid target sequence. In this embodiment, to minimize background, the hybrid is typically purified from the un-annealed nucleic acid prior to the enzyme reaction, which releases identifier nucleotides. A signal confirms the presence of a nucleic acid target sequence that is not totally complementary to the nucleic acid probe.

In an embodiment that uses a 3'→5' exonuclease activity of Exonuclease III to depolymerize a nucleic acid probe, an identifier nucleotide is released when the 3'-terminal residue of the nucleic acid probe is matched to the target nucleic acid. A signal confirms the presence of a nucleic acid target that is complementary at the released identifier nucleotide.

It is thus seen that hybridization and depolymerization can lead to the release of an indicator nucleotide or to little or no release of such a nucleotide, depending upon whether the probe:target hybrid is matched or mismatched at the 3'-terminal region. This is also dependent on the type of enzyme used and the type of end, matched or mismatched, that the enzyme requires for depolymerization activity.

The magnitude of a contemplated analytical output under defined conditions is dependent upon the amount of released nucleotides. Where an identifier nucleotide is released, an analytical output can be provided that has a value greater than background. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level.

Depolymerization reactions and enzymes useful in such reactions are discussed in parental U.S. patent application Ser. No. 09/358,972, filed on Jul. 21, 1999, which disclosure is incorporated herein by reference.

In some preferred embodiments, the reaction conditions are preferably adjusted to further favor depolymerization of a nucleic acid probe that is hybridized with its target nucleic acid sequence by providing a higher concentration of nucleic acid probe than its target nucleic acid sequence.

One strategy to favor the depolymerization of a probe:target hybrid is that the probe be in excess over the nucleic acid target in the hybridization step after denaturing of duplex target nucleic acid.

Another strategy to favor the depolymerization of a probe:target hybrid is to isolate only the strand of nucleic acid target to which the probe is complementary. There are several techniques that can be used to achieve this end.

In one technique, a primer is used that contains a 5'-terminus containing a plurality of nucleotide linkages that are resistant to cleavage by 5' to 3' exonuclease enzymes such as bacteriophage lambda exonuclease (λ exonuclease) and bacteriophage T7 gene 6 exonuclease (T7 exonuclease) and bacteriophage T3 gene 6 exonuclease (T3 exonuclease). Examples of such modified nucleotide derivatives are disclosed by Zon et al., *Anti-Cancer Drug Design* 6:539–568 (1991) and Goodchild et al., *Bionconjugate Chem.* 1:613–629 (1990). In general, suitable nucleotide derivatives include those in which one or two of the non-bridging oxygens of the phosphate moiety of a nucleotide have been replaced with a sulfur-containing group (especially a phosphothioate), an alkyl group (especially a methyl or ethyl alkyl group), a nitrogen-containing group (especially an amine), and/or a selenium-containing group. Preferred phosphodiester replacement linkages include phosphorothioate, phosphorodithioate, methylphosphonate, and phosphoroamidate linkages.

Phosphorothioate linkages are most preferred and are utilized at the 5'-terminus of a target nucleic acid amplifying primer sequence, e.g., at the 1 to about 10 5'-most linkages. The 5'-terminus preferably contains bases that are resistant to cleavage by 5' to 3' T7 gene 6 exonuclease, T3 gene 6 exonuclease, or λ exonuclease. Preferably, the 5'-terminus contains two or more phosphorothioate linkages. More preferably, two to three phosphorothioate linkages are present at the 5'-terminus of an amplification primer.

Interestingly, U.S. Pat. No. 5,518,900 to Nikiforov et al. teaches that four or more phosphorothioate linkages are required for nuclease resistance. However, as is shown in the examples hereinafter, as few as two or three such linkages are also useful.

Upon PCR amplification of the target, the phosphorothioate linkages of the primer become incorporated into the amplified target nucleic acid as part of one of a pair of complementary strands. Treatment of the resulting double-stranded DNA molecule with T7 gene 6 exonuclease, or T3 gene 6 exonuclease, or lambda exonuclease removes the non-phosphorothioate-containing strand. This technique is illustrated in detail in the Examples hereinafter.

In another technique, strand isolation can be accomplished by amplifying the target nucleic acid using PCR primers incorporated into the extended nucleic acid strand (with which a nucleic acid probe useful herein is designed to hybridize) that are not labeled, whereas primers for the complementary strand are labeled, such as with biotin. Then, the amplified nucleic acid is denatured and added to streptavidin linked to a solid support. A useful material is Streptavidin MagneSphere® paramagnetic particles (Promega, Z548A), where a magnet can be used to separate the desired target nucleic acid strand from its biotinylated complementary strand.

Analytical Output

The analytical output is obtained by detection of the released identifier products, either the released nucleotides or the remainder of the probe. Exemplary detection systems include the light emitting luciferase detection system, a fluorescent detection system (including an NADH detection system), absorbance emissions and mass spectrometry. These detection systems are discussed hereinbelow.

The fact that nucleotides were released (a qualitative determination), or even the number of nucleotides released (a quantitative determination) can be deduced through examination of the probe after depolymerization. The determination of the size of an oligonucleotide is well known in the art. For example gel separation and chromatographic separations are well known. Gel imaging techniques that take advantage of fluorescence and absorbance spectroscopy as well as radiographic methods. Mass spectrometry of oligonucleotides is also becoming more common.

Detection of analytical output is disclosed in parental U.S. patent application Ser. No. 09/358,972, filed on Jul. 21, 1999, whose disclosures are incorporated herein by reference.

It is contemplated that an increase in the signal (analytical output) produced by the probe-mediated specific nucleic acid detection methods of the invention can be realized by a novel cycling method. In this embodiment of the invention, two probes are designed that are complementary to each other and have a 3' overhang at each end of the duplex formed when they hybridize to one another. In preferred embodiments, the probes are designed so that the 3' overhang is a single base overhang. In alternative embodiments, the probes also can hybridize to a target nucleic acid. In particularly preferred embodiments, a polymerase that acts from the 3' end of nucleic acids and does not recognize 3' overhangs is utilized for the depolymerization reaction, such as Klenow exo-.

In preferred embodiments, the first step of the reaction involves hybridization of an excess of one of the probes to the target nucleic acid in the presence of the polymerase and under conditions permitting depolymerization as described above. In some embodiments, no 3' overhang exists, and the depolymerase reaction proceeds from the 3' end of the probe. In some embodiments, the reaction is terminated by separating the probe from the target nucleic acid by heating the probe-target nucleic acid complexes. On average, as few as one base is removed from probes that were bound to the target nucleic acid, and fractions of shortened probes are created.

In the second step, an excess of the second probe is added to the reaction. Due to the law of mass action, the shortened probes produced in the first step have a tendency to bind to the newly added complementary probes, whereas the non-shortened probes bind to the target nucleic acid. The shortened probes that bind to the complementary probes produce a complex with no 3' overhang on one end, and are depolymerized. This effectively doubles the amount of substrate available for the depolymerization reaction. Steps one and two can be repeated additional times until the desired level of detection is achieved. In an alternative preferred embodiment, the reactions can be coupled with NDPK as described above, to produce ATP equivalents that are detectable by a luciferase-based or NADH-based assay system.

In some embodiments of the invention, it is preferable that the 3'-terminal region of a probe hybridizes with total complementarity to the nucleic acid target sequence. In some embodiments of the invention, it is preferable that the 3'-terminal region of a probe hybridizes with partial complementarity, even in the case of depolymerization with an enzyme whose maximum activity is to release nucleotides from nucleic acid hybrid having total complementarity. As shown in Example 8, the intentional introduction of a destabilizing base mismatch at one position enhances the discrimination between a match and mismatch at another position.

The first probe has an identifier nucleotide in its 3'-terminal region. The second probe can also contain an identifier nucleotide in its 3'-terminal region. The identifier nucleotide used depends on the desired method of analysis for released nucleotide, as discussed hereinabove.

A hybrid can form between a first probe and the nucleic acid target sequence when the nucleic acid target sequence is present in the nucleic acid sample. Typically, a designed probe that can be the same or different from the first probe and is therefore referred to as the third probe can be added to a nucleic acid sample and permitted to anneal to the designed probe to form a hybrid with the target nucleic acid sequence.

The first reaction mixture also comprises a depolymerizing amount of an enzyme whose activity is to release one or more nucleotides from a 3'-terminus of a hybridized nucleic acid. As discussed hereinabove, the particular enzyme used is based on the substrates to be depolymerized and the goals of the analysis. The first reaction mixture is similar to the above-discussed depolymerization reaction mixtures as far as preferred sample and enzyme concentrations and other reaction conditions.

The first reaction mixture is maintained for a time period sufficient to permit the enzyme to depolymerize hybridized nucleic acid to release an identifier nucleotide from the 3'-terminal region of the first probe, and form a treated reaction mixture. In a contemplated process where the original nucleic acid target is RNA, and the probe is DNA, the effect may be noticed that a DNA/DNA homoduplex is depolymerized at a faster rate or to a greater extent than a DNA/RNA heteroduplex. This effect depends upon the enzyme and its relative affinity for various substrates.

The treated first reaction mixture is denatured by subjecting the treated reaction mixture to denaturing conditions and maintaining the treated reaction mixture for a time period sufficient to denature the nucleic acid hybrids and form a denatured treated reaction mixture. The precise conditions required for denaturation are a function of several factors as is discussed hereinabove. Preferably, the reaction will be heated to a temperature of 90–95° C. for 2–5 minutes.

The denatured treated reaction mixture is subjected to annealing (hybridizing) conditions and maintained for a time period sufficient to form a second reaction mixture that comprises hybrids formed between the first probe and the 3'-terminal-depolymerized third nucleic acid probe. Because of the 3'-terminal depolymerization of the third probe, the hybrid formed with the first probe have one end that is blunt or that has a 5'-overhang (i.e., lacks a 3'-overhang on one end of the duplex). The hybrid formed between the first probe and a nucleic acid target sequence when the nucleic acid target sequence is present in the nucleic acid sample also has a 5'-overhang.

Further depolymerization as before provides a second treated reaction mixture that contains a further quantity of identifier nucleotides in addition to those provided by the first depolymerization step. That further quantity of identifier nucleotides can be about twice the original amount so that the total identifier present is about three-times the original amount.

The second treated reaction mixture is analyzed for the presence of released identifier nucleotide to obtain an analytical output. The analytical output indicates the presence or absence of the single-stranded nucleic acid target sequence.

The first and third probes are preferably the same. Preferably, prior to analysis of the first reaction mixture to detect released identifier nucleotide, the denaturation, annealing and depolymerization steps are repeated to further amplify the number of nucleic acid hybrids from which identifier nucleotides are released.

Not wishing to be bound by theory, it is theorized that in an above process, the first probe (that is complementary to the single-stranded target) is depolymerized, either when it is hybridized to the initial single stranded nucleic acid target sequence or when it is hybridized to its complementary probe sequence. Thus, the effective concentration of target/probe hybrid increases linearly at each progressive cycle of depolymerization. Eventually, a first probe can become too short to hybridize effectively as more and more nucleotides are released from its 3'-terminus.

A related embodiment of the invention contemplates a process to determine the presence or absence of a predetermined double-stranded nucleic acid target sequence. A process differs from the single-strand target process by (i) the presence of a double-stranded nucleic acid target sequence and (ii) third and fourth probes hybridized to separate sequences of DNA that results in an exponential rise in the amount of identifier nucleotide rather than a linear rise as noted before.

As with the single-strand target method, the first and third probes are preferably the same. Preferably, prior to analysis of the amplification reaction mixture to detect released identifier nucleotide, the denaturation, annealing and depolymerization steps are repeated to further amplify the number of nucleic acid hybrids from which identifier nucleotides are released.

It should also be apparent that the single-strand or double strand method can also be carried out by addition of the first and second probes after one has carried out a depolymerization reaction of a treated reaction mixture and before analysis of identifier nucleotides. Both methods are also particularly useful where a before-mentioned thermostable polymerase is used for depolymerization, as well as where a thermostable polymerase and a thermostable NDPK are used in a one-pot reaction.

It is contemplated that in some embodiments, the dNTPs or NTPs produced by pyrophosphorolysis or nuclease digestion are used, in the presence of ADP, to generate XTP, which can then be used directly as substrate for luciferase, permitting detection of the nucleic acid. However, the preferred substrate for luciferase is ATP, as demonstrated by Moyer and Henderson, *Anal. Biochem.*, 131:187–89 (1983). When DNA is the initial substrate, NDPK is conveniently utilized to catalyze the phosphate transfer from dNTPs to ADP to form ATP by the following general reaction:

Reaction 1:

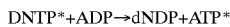

wherein dNTP is a mixture of deoxyribonucleoside triphosphates and DNDP is the corresponding deoxyribonucleoside diphosphate. In Reaction 1, the terminal 5'-triphosphate (P*) of the DNTP is transferred to ADP to form ATP.

Enzymes catalyzing this reaction are generally known as nucleoside diphosphate kinases (NDPKs). NDPKs are ubiquitous, relatively nonspecific enzymes. For a review of NDPK, see Parks and Agarwal, in *The Enzymes*, Volume 8, P. Boyer Ed. (1973).

The use of NTPs or dNTPs, in the presence of ADP, to form ATP by NDPK is preferably accomplished by adding NDPK and a molar excess of ADP over the amounts of NTPs or dNTPs expected to be produced by pyrophosphorolysis or nuclease digestion, followed by pyrophosphorylation by PRPP synthetase. The utilization of ADP requires optimization of the amount of ADP added. Too much ADP results in high background levels.

NDPK (EC 2.7.4.6) preparations from several biological sources are commercially available from several suppliers. For example yeast NDPK is available from Sigma Chemical Co., St. Louis, Mo., whereas bovine NDPK is available from ICN Biochemicals, Inc., Costa Mesa, Calif. The particular NDPK selected for most uses described herein is typically a matter of choice.

Although yeast, bovine or another NDPK can be used in these reactions, it is preferred to utilize a thermostable NDPK such as the Pfu NDPK along with a thermostable depolymerizing enzyme, preferably the Tne triple mutant DNA polymerase (discussed below), Bst DNA polymerase, Ath DNA polymerase, Taq DNA polymerase and Tvu DNA polymerase, most preferably the Tne triple mutant DNA polymerase or Tvu DNA polymerase, along with a reaction temperature of about 50° C. to about 90° C. The use of these thermostable enzymes at an above temperature can enhance the sensitivity of the method.

The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A, D389A).

Briefly, that enzyme is a triple mutant of the polymerase encoded by the thermophilic eubacterium *Thermotoga neapolitana* (ATCC 49049). The amino-terminal 283 residues of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

A reaction containing NDPK contains about 0.01 to 0.50 $\mu$M ADP, preferably about 0.05 $\mu$M ADP. Various useful buffers and other reaction components are set forth elsewhere. NDPK is itself present in an amount sufficient to catalyze the desired conversion of ADP to ATP. In a typical assay starting from a 20 μL depolymerization reaction, about 0.1 U of NDPK are used.

Where larger volumes of reactants are used, with the target and probe concentrations being approximately proportionately larger, the amount of NDPK or the other enzymes discussed herein can be used in a similar larger proportion relative to the amount discussed for the 20 μL reaction. Indeed, a 20 μL reaction has been successfully scaled down about two fold and scaled upwardly by a factor of about 20.

As an optional step, the NTP, DNTP, or ATP generated by the pyrophosphorolysis or nuclease digestion reactions followed by appropriate treatments can be amplified to give even greater sensitivity. For example, amplification can be required when detection systems other than luciferase are utilized or when increased levels of signal are needed for detection by a less sensitive luminometer. "Amplification of NTP" refers to a continuous reaction, wherein 1 NTP gives rise to 2 NTPs, which can be cycled to yield 4 NTPs and so on. When AMP is added to feed the amplification reaction, ATP accumulates. PCT publication WO 94/25619 and Chittock et al., *Anal. Biochem.*, 255:120–6 (1998), incorporated herein by reference, disclose amplification systems for ATP characterized by the following coupled reactions:

Reaction 2:

C1+S1+E1→2C2 and 2C2+2S2+E2→2C1

2C1+2S1+E1→4C2 and 4C2+4S2+E2→4C1

4C1+4S1+E1→8C2 and 8C2+8S2+E2→8C1 wherein C1 is the target compound present in a sample to be amplified, S1 is the amplification substrate, E1 is a catalytic enzyme capable of utilizing C1 and S1 to produce C2, S2 is a high energy phosphate donating substrate, and E2 is a catalytic enzyme capable of utilizing C2 and S2 to produce C1, which then recycles through the reaction. According to this reaction scheme, each pass through the coupled reaction doubles the amount of C1, which can be subsequently detected. Patent Application GB 2,055,200 discloses an amplification system utilizing adenylate kinase and pyruvate kinase.

In providing a coupled ATP amplification reaction for use in nucleic acid detection, two main requirements should be considered. First, E1 should not be able to utilize the high energy phosphate donor utilized by E2. If E1 can utilize the high energy phosphate donor, the ATP amplification reaction proceeds in the absence of NTP or DNTP produced as a result of pyrophosphorolysis. This results in the undesirable occurrence of false positive results. Second, a molar excess of the added high energy phosphate donor is preferably provided as compared to the amount of XTP expected in the reaction. Third, E1 should be able to utilize either the NTP, dNTP, or ATP produced in step 1 by pyrophosphorolysis or nuclease digestion of the nucleic acid.

The amplification system of some preferred embodiments of the present invention can be characterized, as follows:

Reaction 3:

XTP+AMP+E1→XDP+ADP

ADP+D-P+E2→ATP wherein D-P is a high energy phosphate donor and E1 and E2 are enzymes capable of catalyzing the transfer of phosphates from an XTP to AMP and from the D-P to ADP, respectively. The ATP so produced can reenter the reaction (i.e., as XTP) and the reaction can be repeated until the substrates are exhausted or equilibrium is reached, resulting in the production of two ATPs for every ATP supplied to or generated by the reaction. When the target XTP is any nucleoside triphosphate other than ATP, the initial pass through the cycle yields only 1 ATP that then reenters the cycle to produce two ATP, both of which reenter the cycle to produce 4 ATP and so on. Preferably, the amplification reaction produces a threshold ATP concentration of approximately $1 \times 10^{-12}$ Molar in 100 μL of sample.

In some preferred embodiments, the XTP in the amplification system above is NTP or dNTP, which can preferably be ATP provided by pyrophosphorolysis (e.g., depolymerization of RNA by RNA polymerase) or created from XTP by NDPK conversion of ADP to ATP (e.g., Reaction 1) or provided by nuclease digestion coupled with transformation of the XMPs to XTPs (e.g., the reaction catalyzed by PRPP synthetase in the presence of PRPP as the high energy phosphate donor) followed by NDPK conversion to ATP (e.g., Reaction 1. It should be appreciated, however, that when an amplification step is utilized for a DNA substrate, the step of converting dNTP to ATP is inherent in the amplification system. Therefore, a separate converting step is not required for the present invention.

A nucleoside monophosphate kinase (NMPK) or adenylate kinase is preferably utilized as enzyme 1 (E1). NMPKs occur as a family, each of which is responsible for catalyzing the phosphorylation of a particular NMP. Until recently, it was generally thought that ATP and DATP were preferred phosphate donors. However, Shimofuruya and Suzuki *Biochem. Intl.*, 26(5):853–61 (1992) recently demonstrated that at least some NMPKs can utilize other phosphate donors such as CTP and UTP. Enzyme 2 (E2) is preferably NDPK or pyruvate kinase. NDPKs generally catalyze the transfer of the terminal 5'-triphosphate of NTPs to NDPs to form NTPs from the NDP. Pyruvate kinase catalyzes the transfer of phosphate from phosphoenolpyruvate (PEP) to ADP to form ATP. These enzymatic activities are utilized in the amplification reaction to transfer a phosphate group from a high energy phosphate donor (D-P) to either ADP or an NDP.

In particularly preferred embodiments, a high energy phosphate donor (D-P) that can be used by E2 but not by E1 is used. When E2 is NDPK, dCTP or α,β-methylene adenosine 5'-triphosphate (AMP-CPP) can be utilized as D-P. When E2 is pyruvate kinase, PEP is the preferred high energy phosphate donor.

Prior to the invention disclosed in the parent application, the ability of NDPK to utilize these substrates at efficiencies permitting production of minute quantities of ATP was not known. As the recent literature suggests that NMPK (E1) can utilize phosphate donors other than ATP or DATP, it is surprising that these high energy phosphate donors utilized with NMPK meet the requirements of the amplification reaction. The nonspecificity of adenylate kinase is also well known, and in the examples adenylate kinase is E-1, dCTP is not used as D-P.

The high energy phosphate donor and/or AMP is preferably provided in a molar excess as compared to the amount of ATP or dNTP expected to be present in the sample, so that the high energy phosphate donor is not recycled at an appreciable rate. Although it is not intended that the present invention be limited to any particular embodiment, various buffers and reaction components are provided in the Examples.

Coupled Reactions

In some embodiments, certain of the above reactions can be performed as single pot reactions. A "single pot reaction" is a reaction wherein at least two enzymes (i.e., E1 and E2) with catalytic activity are present in the same reaction mix and act on one or more substrate(s) (i.e., S1 and S2). In some embodiments, the reactions catalyzed by the enzymes occur simultaneously where E1 acts on S1 and E2 acts on S2. Alternatively, the reactions catalyzed by E1 and E2 can occur in a step-wise or coupled manner (e.g., where E1 acts on S1 to produce an intermediate $S2_i$, and E2 then acts on $S2_i$). Of course, in yet other embodiments, such a coupled reaction can also be essentially simultaneous.

The ability to utilize combinations or mixtures of the enzymes of the present invention in single pot reactions is surprising, in light of the extremely low levels of nucleic acid detection that are achieved using the present invention. This low level detection is possible even though some enzymes are used under suboptimal conditions. As previously described, it was found to be necessary to optimize the concentration of $PP_i$ utilized in the pyrophosphorolysis reactions to minimize inhibition of luciferase. Therefore, aliquots from the NMP-, dNMP-, NTP-, dNTP- and ATP-producing reactions can be directly added to L/L Reagent for luciferase detection without any purification of the reaction products. The luciferase reaction is not poisoned or otherwise quenched by the components of the reactions. This desirable feature permits automation and high throughput analysis with a minimal amount of time and effort, and it also permits great flexibility in the design of the overall detection schemes. However, it is not intended that the present invention be limited to any particular reaction condition, reagents, or embodiments.

In some preferred embodiments, the pyrophosphorolysis reaction producing DNTP and the NDPK catalyzed reaction in which the NTPs or dNTPs are converted to ATP are performed in a single pot reaction in the nucleic acid polymerase buffer in these embodiments. NDPK activity is sufficient to convert dNTP to ATP, even though the polymerase buffer conditions are suboptimal for NDPK activity.

The polymerase enzyme and NDPK can both be present initially in the reaction, or the NDPK can be added directly to the reaction after an incubation period sufficient for the production of NTP or dNTP. Alternatively, a nucleic acid polymerase and NDPK can be provided in the same vessel or mixture for use in the reactions described above. The mixture preferably contains the nucleic acid polymerase and NDPK in a concentration sufficient to catalyze the production of ATP when in the presence of a nucleic acid, pyrophosphate and ADP.

Preferably, the polymerase is provided in a concentration of about 0.1 to 100 U/reaction (i.e., where "U" is units) most preferably at about 0.5 U/reaction. Preferably, the NDPK is provided in a concentration of 0.1 to 100 U/reaction, most preferably at about 0.1 U/reaction. In further preferred embodiments, the mixture is substantially free of contaminating ATP.

Similarly, the PRPP synthetase and NDPK reactions can be carried out in a single pot reaction in the PRPP synthetase buffer. Again, in these embodiments, NDPK activity is sufficient even though conditions for NDPK activity are suboptimal.

The nuclease-digested sample containing free NMPs and dNMPs can be added to a reaction mix initially containing PRPP synthetase and NDPK, or added to a PRPP synthetase reaction followed by addition to a reaction mix containing NDPK. By way of example, certain preferred buffers and reaction components can be found in the Examples. However, it is not intended that the present invention be limited to specific buffers or reaction components.

PRPP synthetase and NDPK can be provided in the same vessel or mixture for use in the reactions described above. The mixture preferably contains the PRPP synthetase and NDPK in a concentration sufficient to catalyze the production of ATP when in the presence of PRPP and ADP. Preferably, the NDPK is provided in a concentration of 0.1 to 100 U/reaction, most preferably at about 0.1 U/reaction. Preferably, the PRPP synthetase is provided in a concentration of 0.001 to 10 U/reaction, most preferably at about 0.01 U/reaction. If amplification is desired, the PRPP synthetase reaction is preferably heat inactivated, otherwise the PRPP synthetase converts the added AMP to ATP.

The pyrophosphorolysis reaction and amplification reaction can also be performed in a single pot reaction. In this single pot reaction, poly(A) polymerase or any suitable template-dependent polymerase can be used, including, but not limited to, AMV reverse transcriptase, MMLV reverse transcriptase, DNA polymerase alpha or beta, Taq polymerase, Tth polymerase, Tne polymerase, Tne triple mutant polymerase, Tvu polymerase, Ath polymerase, E. coli DNA polymerase I, T4 DNA polymerase, Klenow fragment, Klenow exo minus, or poly (A) polymerase.

In some embodiments, a first enzyme for converting AMP to ADP can be myokinase (e.g., adenylate kinase) or NMPK, and in other embodiments, a second enzyme for converting ADP to ATP can be pyruvate kinase or NDPK. In addition, in preferred embodiments, the reaction is fed AMP. In particularly preferred embodiments, apyrase-treated AMP is utilized to reduce background due to contaminating ADP and ATP. Preferably 1 μL of 1 U/μL apyrase is added to 19 μL of 10 mM AMP, followed by incubation at room temperature for 30 minutes and heat inactivation of the apyrase by incubation at 70° C. for 10 minutes.

High energy phosphate donors are also added to the reaction. In preferred embodiments, when pyruvate kinase is utilized, PEP is added. In other preferred embodiments, when NDPK is utilized, dCTP is added. Preferably, the high energy phosphate donor is added about 15 minutes after a pre-incubation with the polymerase, although this is not necessary. These reactions can be characterized as follows:

Reaction 4:

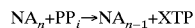

$$NA_n + PP_i \rightarrow NA_{n-1} + XTP$$

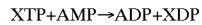

$$XTP + AMP \rightarrow ADP + XDP$$

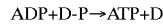

$$ADP + D\text{-}P \rightarrow ATP + D$$

wherein NA is a nucleic acid, XTP is a nucleoside triphosphate (either a deoxynucleoside or ribonucleoside triphosphate), XDP is a nucleoside diphosphate (either a deoxynucleoside or ribonucleoside diphosphate), and D-P is a high energy phosphate donor. It should be appreciated that this reaction produces ATP, the preferred substrate for luciferase, from dNTPs.

The amplification reaction proceeds as described in reaction 4 to produce a threshold ATP concentration of approximately $1 \times 10^{-12}$ Molar in 100 μL of sample. Preferably, the polymerase is provided in a concentration of about 0.1 to 100 U/reaction, most preferably at about 0.5 U/reaction. Preferably, the NDPK is provided in a concentration of 0.1 to 100 U/reaction, most preferably at about 0.1 U/reaction. Preferably, the mixture is substantially free of contaminating ATP.

Kits

Other embodiments of the invention contemplate a kit for determining the presence or absence of a predetermined nucleic acid target sequence in a nucleic acid sample. Such a kit comprises an enzyme whose activity is to release one or more nucleotides from the 3' terminus of a hybridized nucleic acid probe and at least one nucleic acid probe, said nucleic acid probe being complementary to nucleic acid target sequence.

The kit optionally further comprises a nucleoside diphosphate kinase. Preferably, the nucleoside diphosphate kinase is that encoded by *Pyrococcus furiosis*. The kit optionally further comprises instructions for detecting said nucleic acid by depolymerization. Preferably the enzyme whose activity is to release nucleotides in the kit is a template dependent polymerase that, in the presence of pyrophosphate ions, depolymerizes hybridized nucleic acids whose bases in the 3'-terminal region are matched with total complementarity. Alternatively, the enzyme whose activity is to release nucleotides in the kit exhibits a 3' to 5' exonuclease activity, depolymerizing hybridized nucleic acids having one or more mismatched bases at the 3' terminus of the hybridized probe.

It is to be understood that such a kit is useful for any of the methods of the present invention. The choice of particular components is dependent upon the particular method the kit is designed to carry out. Additional components can be provided for detection of the analytical output, as measured by the release of identifier nucleotide, or by detection of the remaining probe after depolymerization. For example, ethidium bromide can be provided in the kits of the invention for detection of a probe that has had identifier nucleotide released from the 3'-terminal region.

The instructions present in such a kit instruct the user on how to use the components of the kit to perform the various methods of the present invention. These instructions can include a description of the detection methods of the invention, including detection by luminescence spectroscopy, mass spectrometry, fluorescence spectroscopy, and absorbance spectroscopy.

In another embodiment, the invention contemplates a kit for determining the presence or absence of at least one predetermined nucleic acid target sequence in a nucleic acid sample comprising the following components: an enzyme whose activity in the presence of pyrophosphate is to release identifier nucleotide as a nucleoside triphosphate from hybridized nucleic acid probe; adenosine 5' diphosphate; pyrophosphate; a nucleoside diphosphate kinase; and at least one nucleic acid probe, wherein the nucleic acid probe is complementary to the predetermined nucleic acid target sequence.

Preferably, the enzyme whose activity in the presence of pyrophosphate is to release identifier nucleotides is the Tne triple mutant DNA polymerase, Klenow exo-, Klenow, T4 DNA polymerase, Ath DNA polymerase, Taq DNA polymerase and Tvu DNA polymerase, most preferably Tne triple mutant DNA polymerase, Klenow exo-, or Tvu DNA polymerase. In an alternative embodiment, a thermostable polymerase is preferred, wherein in the thermostable polymerase is preferably the Tne triple mutant DNA polymerase, T4 DNA polymerase, Ath DNA polymerase, Taq DNA polymerase and Tvu DNA polymerase, most preferably Tne triple mutant DNA polymerase, or Tvu DNA polymerase. Preferably, the nucleoside diphosphate kinase is that encoded by *Pyrococcus furiosis*. The kit optionally comprises instructions for use.

In another embodiment, the invention contemplates a kit for determining the presence or absence of a predetermined nucleic acid target sequence in a nucleic acid sample comprising an enzyme whose activity is to release one or more nucleotides from the 3' terminus of a hybridized nucleic acid probe and instructions for use. Such a kit optionally comprises a nucleoside diphosphate kinase. Preferably, the nucleoside diphosphate kinase is that encoded by *Pyrococcus furiosis*. The kit further optionally comprises a nucleic acid probe complementary to the predetermined nucleic acid target sequence.

In other embodiments of the present invention, nucleic acid detection test kits are provided for performing a depolymerization method contemplated by this invention, and particularly a depolymerization detection method.

In one embodiment, the kit includes a vessel containing an enzyme capable of catalyzing pyrophosphorolysis, including, but not limited to Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase, preferably a thermostable polymerase, most preferably Tne triple mutant polymerase or Tvu polymerase. In another embodiment, the kit contains a vessel that contains an exonuclease such as S1 nuclease, nuclease BAL 31, mung bean nuclease, exonuclease III and ribonuclease H.

Either of the above enzyme types is utilized in a contemplated method in a depolymerizing effective amount. That is, the enzyme is used in an amount that depolymerizes the hybridized probe to release an identifier nucleotide. This amount can vary with the enzyme used and also with the temperature at which depolymerization is carried out. An enzyme of a kit is typically present in an amount of about 0.1 to 100 U/reaction; in particularly preferred embodiments, the concentration is about 0.5 U/reaction. An amount of enzyme sufficient to carry out at least one assay, with its controls is provided.

As noted elsewhere, the preferred analytical output for determining the presence or absence of identifier nucleotide is luminescence caused by the reaction of ATP with luciferin in the presence of luciferase. A kit containing a pyrophosphorylation enzyme for use in DNA detection using luminescence also preferably includes a vessel containing NDPK and a vessel containing ADP. Similarly, a kit containing an exonuclease enzyme for use in DNA detection using luminescence also preferably includes a vessel containing PRPP synthetase and a vessel containing ADP. The NDPK or PRPP synthetase is provided in concentration of about 0.01 to 100 U/reaction, preferably about 0.1 to about 1.0 U/reaction.

Preferably, these reagents, and all of the reagents utilized in the kits discussed herein, are free of contaminating ATP and adenylate kinase. Some of the contaminants can be removed from the enzymes by dialysis treatment.

Optionally, the kit contains vessels with reagents for amplification of dNTPs or NTP to ATP. Amplification reagents include, but are not limited to pyruvate kinase, adenylate kinase, NMPK, NDPK, AMP (e.g., as the amplification enzymes and substrate), and dCTP or AMP-CPP (e.g., as high-energy phosphate donors). In particularly preferred embodiments, the kit can be packaged in a single enclosure including instructions for performing the assay methods. In some embodiments, the reagents are provided in containers and are of a strength suitable for direct use or use after dilution. In alternative preferred embodiments, a standard set can also be provided in order to permit quantification of results. In yet other preferred embodiments, test buffers for optimal enzyme activity are included.

In yet other embodiments, a contemplated kit comprises a nuclease, PRPP synthetase, PRPP, NDPK, and ADP together with luciferase and luciferin. In preferred embodiments, the nuclease is provided in a concentration of about 1 to 500 U/reaction; in particularly preferred embodiments at a concentration of about 20 U/reaction. In a particularly preferred embodiment, the PRPP synthetase is provided in concentration of about 0.01 U/reaction to 10 U/reaction, preferably about 0.1 U/reaction. In some preferred embodiments, the kit includes all these reagents with luciferase and luciferin being provided as a single reagent solution.

In other preferred embodiments, these reagents include, but are not limited to, a high energy phosphate donor which cannot be utilized by luciferase, preferably dCTP, and AMP together with luciferase and luciferin. In alternative preferred embodiments, the kit includes all these reagents with luciferase and luciferin being provided in the same solution.

In still further embodiments of the present invention, the kits described above can contain a probe or probes for probe-mediated specific nucleic acid detection. In some embodiments, the kit contains at least one nucleic acid probe for a nucleic acid target of interest. In other embodiments, the kits contain multiple probes, each of which contain a different base at an interrogation position or which are designed to interrogate different target DNA sequences.

In each of the embodiments, the kits contain instructions for use in interrogating the identity of a specific base within a nucleic acid target, for discriminating between two homologous nucleic acid targets that differ by one or more base pairs, or for determining whether a nucleic acid target contains a deletion or insertion mutation. The types of nucleic acid probes that can be included in the kits and their uses are described in greater detail below.

EXAMPLE 1

Use of Chemical DNA Denaturation of Target DNA Prior to Genotype Determination In this Example, denaturation of target DNA by chemical agents is compared to high temperature denaturation.

An amplified DNA segment containing a segment of the Factor V gene in the region of the Leiden mutation, but from wild type served as the targets in this Example.

The amplified DNA was purified using Wizard PCR Preps (Promega A7170) by mixing 25 $\mu$L PCR product with 1 mL resin and washing with 3×1 mL 80% isopropanol. Probe FV7 (SEQ ID NO:1) and FV8 (SEQ ID NO:2) were used, and the following solutions were assembled.

| Solution | Target* ($\mu$L) | Probe ($\mu$L) | Water ($\mu$L) | Total ($\mu$L) |
|---|---|---|---|---|
| 1 and 2 | 4 | 1, FV7 150 (pmol) | 15 | 20 |
| 3 and 4 | 4 | 1, FV8 | 15 | 20 |
| 5 | 4 | none | 15 | 20 |
| 6, 7, 11, 12, 16, and 17 | 4 | 1, FV8 | 4 | 9 |
| 8, 9, 13, 14, 18 and 19 | 4 | 1, FV7 | 4 | 9 |
| 10, 15, and 20 | 4 | none | 5 | 9 |

Solutions 1–5 were heated at 95° C. for three minutes then put in a 37° C. incubator for 10 minutes. Solutions 6–10 were treated with 1 $\mu$L 0.2 N sodium hydroxide for 1–2 minutes, then 10 $\mu$L water were added. Solutions 11–15 were treated with 1 $\mu$L 0.2 N sodium hydroxide for 1–2 minutes, then 10 $\mu$L 50 mM Tris HCl pH 7.3 were added. Solutions 16–20 were treated with 1 $\mu$L 0.2 N sodium hydroxide for 1–2 minutes, then 10 $\mu$L 100 mM Tris HCl pH 7.3 were added. After these treatments, solutions 7–18 were placed in a 37° C. incubator for 5 minutes.

The following master mix was assembled and mixed.

| Component | Amount |
|---|---|
| 10 X DNA Pol Buffer (Promega, M195A) | 200 $\mu$L |
| Klenow exo- (1 U/$\mu$L) (Promega M218B) | 12.5 $\mu$L |
| 40 mM Sodium Pyrophosphate (Promega C350B) | 25 $\mu$L |
| NDPK (1 U/$\mu$L) | 10 $\mu$L |
| 10 uM ADP (Sigma A5285) | 20 $\mu$L |
| Water | 732.5 $\mu$L |

After the treatments described above, 20 $\mu$L of master mix were added to solutions 1–18 and the solutions were then incubated for 15 minutes at 37° C. After this incubation, the contents of the tubes were added to 100 $\mu$L L/L reagent (Promega F202A) and the light production from the reactions was read immediately using a Turner® TD 20/20 luminometer. The following results were obtained.

| Solution | Relative Light Units | Net Average Light Units |
|---|---|---|
| 1 | 1495 | 1343 |
| 2 | 1540 | |
| 3 | 278.7 | 100.1 |
| 4 | 269.5 | |
| 5 | 174 | 0 |
| 6 | 625 | 1383.2 |
| 7 | 1539 | |
| 8 | 305.1 | 106.9 |
| 9 | 306.3 | |
| 10 | 198.8 | 0 |
| 11 | 1629 | 1408.8 |
| 12 | 1638 | |
| 13 | 304.9 | 82.15 |
| 14 | 308.8 | |
| 15 | 224.7 | |
| 16 | 1595 | 1350.2 |
| 17 | 1567 | |
| 18 | 303.2 | 76.95 |
| 19 | 312.3 | |
| 20 | 230.8 | 0 |

These data indicate that either chemical denaturation or heat denaturation can be used prior to primer pyrophosphorylation without greatly affecting the results.

```
FV7  5' GACAAAATACCTGTATTCCTCG 3'     SEQ ID NO:1

FV8  5' GACAAAATACCTGTATTCCTTG 3'     SEQ ID NO:2
```

EXAMPLE 2

Reduction of Target Background By Removal of One Strand of a Double Strand DNA Target A particular target produced by amplification of a segment of the rice genome is interrogated in this Example. It was found that this target produces high background signal values if nothing is done to eliminate one strand of the amplified DNA target and did not exhibit discrimination between two primers that were designed to detect a SNP present in some rice strains. This Example illustrates how one can purposefully destroy one of the amplified DNA strands and interrogate the other strand. For this case in particular, such manipulations result in greatly reduced background light signals from the target, permitting clear determination of the interrogation signals.

Probes RS1 (SEQ ID NO:3) and RS2 (SEQ ID NO:4) were dissolved at a concentration of 50 pmole/μL in water. Probe RS1 contained phosphorothioate linkages at the first three 5'-terminal linkages that are not cleaved by the enzyme used in the reaction. DNA was isolated from rice and was at a concentration of 10 μg/mL. The following solution was assembled in duplicate:

| Component | Volume (μL) |
| --- | --- |
| 10 X DNA Polymerase buffer without MgCl$_2$ (Promega M190A) | 5 |
| 25 mM MgCl$_2$ (Promega A351A) | 3 |
| 10 mM dNTP mixture (Promega C114A) | 1 |
| Primer RS1 (50 pmol/μL) | 1 |
| Primer RS2 (50 pmol/μL) | 1 |
| Rice genomic DNA (10 ng/μL) | 1 |
| Water | 38 |
| Taq DNA Polymerase (Promega M186A) | 1.25U |

These solutions were heated to 94° C. for two minutes, then subjected to the following temperature cycling program for 35 cycles: 0.5 minutes, 94° C.; 1 minute, 60° C.; 1 minute, 70° C. Then the solution was held at 70° C. for 7 minutes then cooled to 4° C.

The two reaction tubes were pooled and mixed and then 3–25 μL samples were removed and placed into individual tubes. The compositions within the individual tubes were treated with T7 Exonuclease 6 (USB, E700254) as follows.

| | |
| --- | --- |
| Solution 1 | No Exo 6 addition or further heating |
| Solution 2 | 50 U of Exo 6 and heated for 15 minutes at 37° C. |
| Solution 3 | 50 U of Exo 6 and heated for 30 minutes at 37° C. |

The DNA in the resulting solutions was purified using the following method:

1. 200 μL of a slurry containing 15 μL MagneSil™ paramagnetic particles (Promega) in solution containing 0.4 M guanidine thiocyanate and 0.08 M potassium acetate were added to each sample.
2. The MagneSil™ paramagnetic particles were mixed in the solutions and held against the side of the tube with a magnet.
3. The particles were washed twice with 200 μL of 70% ethanol by addition of the solution to the tubes, resuspension of the particles in the solution, recapture of the particles against the tube walls with the magnet and removal of the particle-free solution.
4. The particles were resuspended in fifty microliters of water.
5. 200 μL 0.4 M GTC and 0.08 M potassium acetate were added to each.
6. Step 2 was repeated as described above except that three washes with 70% ethanol were performed.
7. The particles were resuspended in 100 μL water, the particles were captured against the side of the tube, and the solution containing the purified DNA was transferred to a new tube.

A master mix was made as described in Example 1, and primers RS3 (SEQ ID NO:5) and RS4 (SEQ ID NO:6) were resuspended at a concentration of 1 mg/mL in water. Each of the purified DNAs was assembled into reaction solutions as described below.

| Solution | Probe (μL) | Purified DNA Target (μL) | Water (μL) |
| --- | --- | --- | --- |
| Wild Type (WT) Probe | 1, RS3 | 4 | 15 |
| Variant Probe | 1, RS4 | 4 | 15 |
| No Probe | none | 4 | 16 |

These solutions were heated at 95° C. for 3 minutes, then placed in a 37° C. incubator for 10 minutes. After the 10 minute incubation, 20 μL of master mix were added to all tubes and the tubes were incubated again for 15 minutes at 37° C. After this second incubation, the solutions were added to 100 μl of L/L reagent (Promega, F202A) and the light produced measured immediately using a Turner® TD 20/20 luminometer.

The following results were obtained:

| | Relative Light Units Measured | | |
| --- | --- | --- | --- |
| Target | WT Probe | Variant Probe | No Probe |
| No Exo 6 Treatment | 759.0 | 776.0 | 401.6 |
| 15 min. Exo 6 Treatment | 556.6 | 138.4 | 122.3 |
| 30 min. Exo 6 Treatment | 543.2 | 257.4 | 203.0 |

| Calculation of Net Light Units and Ratio of Response Net Light Units* | | | |
| --- | --- | --- | --- |
| Target | WT Probe | Variant Probe | Ratio** |
| No Exo 6 Treatment | 357.4 | 374.4 | 0.95 |
| 15 min. Exo 6 Treatment | 434.3 | 16.1 | 27.0 |
| 30 min. Exo 6 Treatment | 340.2 | 54.4 | 6.25 |

*Net light units are calculated by subtracting the no probe value from the other two values
**Ratio is calculated by dividing the net light units for the WT probe by the net light units for the variant reaction.

The exonuclease used in this example hydrolyzes double-stranded DNA in a 5' to 3' direction, but cannot hydrolyze the DNA if phosphorothioate linkages are present on the 5' end of the DNA to be digested. Thus, the treatment used above should eliminate one strand of the amplified DNA made by extension of primer RS2 but should not eliminate the strand made by extension of primer RS1. This treatment both reduced the response of reactions without primer and permitted the discrimination of the SNP at the interrogation site.

```
RS1  5'C*C*C*A*ACACCTTACAGAAATTAGC 3'      SEQ ID NO:3

(* signifies the presence of a phosphorothioate linkage between the indicated bases.)

RS2  5'TCTCAAGACACAAATAACTGCAG 3'           SEQ ID NO:4

RS3  5'AGAACATCTGCAAGG 3'                    SEQ ID NO:5

RS4  5'AGAACATCTGCAAGT 3'                    SEQ ID NO:6
```

EXAMPLE 3

Improvement in Allele Discrimination by Varying Reaction Conditions and ATP Stability in the Pyrophosphorylation Solution After Pyrophosphorolysis As shown in several examples, pairs of probes can be used to determine the genotype of a DNA segment using coupled enzymatic reactions. One way to present the discrimination of different alleles using this technology is to report the relative detection signals as a ratio, as shown in the Example 2. In this example, a study is described that illustrates that the ratio between the signals from matched and mismatched probes can be varied by alteration of the reaction conditions. In addition, the reaction solutions are incubated on ice to demonstrate that determining the amounts of ATP generated following pyrophosphorylation of the probes does not have to be performed immediately if the solutions are placed on ice.

Oligonucleotides CV1 (SEQ ID NO:7), CV2 (SEQ ID NO:8), and CV3 (SEQ ID NO:9) were dissolved to 1 mg/mL in water and CV3 was diluted to a concentration of 0.3 µg/mL in water. Oligonucleotide CV1 was designed to match a known sequence in the CMV viral genome. Oligonucleotide CV2 was designed to match the same region of the viral genome, but to hybridize exactly to a known drug resistance form of the virus that contained single base changes in this region. Oligonucleotide CV3 was designed to match a larger region of this viral DNA and is used as a target for the hybridization of probes CV1 and CV2 in the study below.

Nine samples of each of the three following solutions were assembled: Solution 1:18 µL water, 1 µL CV3 and 1 µL CV1; Solution 2:18 µL water, 1 µL CV2 and 1 µL CV3; and Solution 3:19 µL water, 1 µL CV3. These solutions were heated at 91° C. for 5 minutes, then cooled at room temperature for 10 minutes.

Three solutions of Klenow exo- were prepared by mixing the following:

| Component | Enzyme solutions | |
|---|---|---|
| | Klenow #1 | Klenow #2 |
| 1 X DNA Polymerase Buffer* | 4 µL | 8 µL |
| Klenow Exo Minus (Promega M218B) | 6 µL | 2 µL |

*Made by 1:10 dilution of Promega 10X DNA Polymerase Buffer (M195A with water).

These manipulations produced solutions of Klenow exo- at concentrations of 6 U/µL and 2 U/µL for the Klenow #1 and Klenow #2 solutions, respectively.

A master mix was made by assembling the following:

| Component | Amount (µL) |
|---|---|
| 10 X DNA Polymerase Buffer | 120 |
| water | 432 |
| 10 mM Sodium Pyrophosphate | 15 |
| NDPK (1 U/µL) | 6 |
| 10 µM ADP (Sigma) | 12 |

After mixing, 195 µL samples of master mix were placed into each of three separate 1.5 mL microfuge tubes labeled MM#1, MM#2 and MM#3, and 5 µL of Klenow exo minus, Klenow #1 and Klenow #2, as described above, were added to those tubes. Twenty microliter samples of each of those mixes were separately added to each of: 3 tubes of solution 1, three tubes of solution 2 and three tubes of solution 3 after the before-described solutions had cooled to room temperature. The tubes were then incubated at 37° C. for 15 minutes. Four microliters of the solution in each tube were immediately added to 100 µL of L/L reagent (Promega F202A) and the light production of the resulting solution was read immediately using a Turner® TD 20/20 luminometer. The tube containing the remaining solution was placed on ice. Periodically, four microliter samples of the remaining solution in each of the tubes were added to 100 µL of L/L reagent (Promega F120B) and the light production of the resulting solution read as before to determine if the values first seen changed over time. The average values for the triplicate readings are given below.

| Reading Time* (min) | CV1/CV3 Reactions | CV2/CV3 Reactions | No Probe Reactions | Ratio** |
|---|---|---|---|---|
| Klenow used: 5 U/reaction | | | | |
| Zero | 235.4 | 31.1 | 2.98 | 8.26 |
| 15 | 231.9 | 30.2 | 2.76 | 8.40 |
| 30 | 233.8 | 32.2 | 3.41 | 8.00 |
| 45 | 219.7 | 32.8 | 8.60 | 8.77 |
| 60 | 218.5 | 31.8 | 4.41 | 7.87 |
| Klenow used: 3 U/reaction | | | | |
| Zero | 200.8 | 26.3 | 6.27 | 9.80 |
| 15 min | 207.2 | 31.9 | 14.9 | 11.2 |
| 30 min | 191.3 | 26.3 | 7.30 | 9.71 |
| 45 min | 202.0 | 26.7 | 6.34 | 9.62 |
| 60 min | 192.8 | 25.9 | 6.03 | 9.43 |
| Klenow used: 1 U/reaction | | | | |
| Zero | 217.5 | 24.6 | 8.03 | 12.65 |
| 15 | 206.8 | 35.5 | 23.8 | 15.9 |
| 30 | 200.0 | 24.4 | 9.24 | 12.7 |
| 45 | 210.7 | 24.9 | 5.70 | 10.6 |
| 60 | 210.7 | 24.5 | 6.12 | 11.1 |

-continued

| Reading Time* (min) | CV1/CV3 Reactions | CV2/CV3 Reactions | No Probe Reactions | Ratio** |
|---|---|---|---|---|

*Reading time = time from placement of the tube on ice post 37° C. incubation.
**Ratio = ratio obtained by dividing the average net CV1/CV3 reaction value by the average net CV2/CV3 reaction value. Net reaction values were calculated by subtracting the no probe reaction value from the value obtained with the indicated probe.

The ratio calculated above provides a measurement of the relative strength of the signals of perfectly matched versus mismatched probes at different enzyme levels. Because the ratio is higher as the amount of enzyme decreased, improved specificity of detection is seen at the lower enzyme amounts used than at the higher amounts used. Because the absolute signal strength of the matching probe/target substrate does not vary much over the enzyme levels used, these data illustrate that one way to improve detection specificity is through the optimization of enzyme concentrations and that the optimal concentration for the enzyme Klenow exo- can be at or below 1 U/reaction in some cases.

The readings, taken up to an hour after the placement of the reaction tubes on ice, do not show much change versus those read immediately. These results suggest that the ATP level in the reactions does not need to be measured immediately but that the measurement can be performed up to at least one hour post incubation if the solutions are placed on ice.

CV1 5' CACTTTGATATTACACCCATG 3'   SEQ ID NO:7

CV2 5' CACTTTGATATTACACCCGTG 3'   SEQ ID NO:8

CV3
5' CGTTGTGCGGGTTCACGTCGATGAGCACGTTCATGGGTGTAATATCAAAGT   SEQ ID NO:9
GGCATACACGAGCT 3'

EXAMPLE 4

Improved Allele Discrimination with Automated ATP Measurement

Improved allele discrimination is demonstrated in this example by varying reaction conditions. In addition, the ability to automate the reading of the samples by the use of a plate luminometer that can add the needed reagent is illustrated.

Oligonucleotides FV1 (SEQ ID NO:10), FV2 (SEQ ID NO:11), FV5 (SEQ ID NO:12) and FV6 (SEQ ID NO:13) were dissolved in water at 1 mg/mL, and then FV1 and FV2 were diluted to 0.3 µg/mL in water. Solution FV1+2 is assembled from equal volumes of the diluted FV1 and FV2. FV1 and FV2 are complementary strands of a segment of the wild type Factor V gene except for a 3' overhang region of FV2. FV5 is an oligonucleotide probe spanning the wild type Factor V gene in the region where the Factor V Leiden mutation occurs in the mutant gene. FV6 is an oligonucleotide probe spanning the same region as FV5, but it is totally complementary to the Factor V mutant. Oligonucleotide FV5 is complementary to a region of FV1 and oligonucleotide FV6 is complementary to FV2. FV5 and FV6 are the interrogation oligonucleotides.

Six replicates of the solutions below were assembled.

| Solution | FV5 (µL) | FV6 (µL) | FV1 + 2 (µL) | Water (µL) |
|---|---|---|---|---|
| Solution #1 | 1 | none | 1 | 18 |
| Solution #2 | none | 1 | 1 | 18 |
| Solution #3 | none | none | 1 | 19 |
| Solution #4 | 1 | none | none | 19 |
| Solution #5 | none | 1 | none | 19 |
| Solution #6 | none | none | none | 20 |

These solutions were heated at 91° C. for 7 minutes and cooled at room temperature for 15 minutes.

The following master mix was assembled.

|  | (µL) |
|---|---|
| 10 X DNA Polymerase Buffer (Promega M195A) | 160 |
| 40 mM Sodium Pyrophosphate (Promega L350B) | 20 |
| NDPK (1 U/µL) | 8 |
| 10 µM ADP (Sigma) | 16 |
| water | 556 |

This solution was mixed and three 253 µL samples were put into separate 1.5 mL microfuge tubes. Enzyme dilutions of Klenow exo- to concentrations of 5 and 2.5 U/µL were made as in Example 3.

A 13.5 µL aliquot of Klenow exo- at 10, 5 and 2.5 U/µL (the lower enzyme concentrations were produced by dilution of stock enzyme) was added to each of the master mix samples. Each resulting solution was mixed and 20 µL samples of the resulting solutions were added to two of each of the 6 different solutions heated at 95° C. before and cooled by incubation at room temperature. The resulting reaction solutions were heated at 37° C. for 15 minutes and then placed on ice.

A microtiter plate was taken and 5 µL samples of nanopure water (controls) added to multiple wells and replicate 5 µL samples of the various reaction mixes corresponding to the reactions performed at one enzyme concentration were also added to individual wells in the plate. The plates were then placed on ice. In total, four replicates of two separate sets of each reaction were put on the plate. In the same way, two additional plates were assembled with the other reaction mixes for the other two enzyme concentrations. The plates were then read on a Luminoskan® luminometer that was programmed to add 100 µL of L/L reagent (Promega F202A) and immediately measure the luminescence produced.

In addition, 5 µL samples of the reaction mixes on ice were read in triplicate using a Turner® TD20/20 luminometer by adding the sample to a tube containing 100 µL of L/L reagent and immediately reading the light production of the resulting solution.

The averages of the data for the results obtained were calculated and are presented below. Samples labeled 'match' contain FV1+2 wild type target and FV5 wild type interrogation probe, previously described as solution #1. Samples labeled 'mismatch' contain FV1+2 wild type target and FV6 mutant interrogation probe, previously described as solution #2.

| Sample | Luminoskan Average Readings Relative Light Units | Ratio* | Turner ® TD 20/20 Average Readings Relative Light Units | Ratio* |
|---|---|---|---|---|
| 10 U Klenow Data | | | | |
| Match #1 | 76.55 | | 179.8 | |
| Match #2 | 71.46 | | 210.7 | |
| Mismatch#1 | 3.90 | | 11.16 | |
| Mismatch#2 | 4.61 | 40 | 11.71 | 52 |
| Target #1 | 1.70 | | 5.32 | |
| Target #2 | 1.51 | | 5.16 | |
| Probe FV1#1 | 3.89 | | 13.73 | |
| Probe FV1#2 | 3.82 | | 11.75 | |
| Probe FV2#1 | 2.54 | | 7.63 | |
| Probe FV2#2 | 2.22 | | 7.06 | |
| No DNA#1 | 1.61 | | 4.37 | |
| No DNA#2 | 1.31 | | 4.90 | |
| 5 U Klenow Data | | | | |
| Match #1 | 59.33 | | 196.0 | |
| Match #2 | 75.59 | | 215.5 | |
| Mismatch#1 | 3.60 | | 11.28 | |
| Mismatch#2 | 3.47 | 54 | 10.17 | 43 |
| Target #1 | 1.77 | | 5.21 | |
| Target #2 | 1.56 | | 4.73 | |
| Probe FV1#1 | 3.13 | | 9.89 | |
| Probe FV1#2 | 3.12 | | 9.33 | |
| Probe FV2#1 | 2.19 | | 6.01 | |
| Probe FV2#2 | 2.22 | | 6.32 | |
| No DNA#1 | 1.58 | | 4.17 | |
| No DNA#2 | 1.46 | | 4.21 | |
| 2.5 U Klenow Data | | | | |
| Match #1 | 68.83 | | 235.6 | |
| Match #2 | 72.20 | | 245.8 | |
| Mismatch#1 | 3.08 | | 9.18 | |
| Mismatch#2 | 3.33 | 72 | 9.83 | 71 |
| Target #1 | 1.90 | | 5.11 | |
| Target #2 | 1.65 | | 4.35 | |
| Probe FV1#1 | 3.11 | | 9.70 | |
| Probe FV1#2 | 2.12 | | 10.99 | |
| Probe FV2#1 | 2.07 | | 5.79 | |
| Probe FV2#2 | 2.12 | | 6.08 | |
| No DNA#1 | 1.62 | | 4.14 | |
| No DNA#2 | 1.59 | | 4.64 | |

*See the text below.

The ratios reported in this example were determined by first averaging the results from matching samples then determining the net light production from the matching and mismatching samples and dividing the net light production from the matching reaction by that seen in the mismatch reaction. The net light production was determined by subtracting the estimated light contribution from the probes and target present in the reactions from the total light produced. The light production from the target reaction was considered to be the total of that contributed from the target specifically and that contributed by contaminating ATP from various components. The net increase from the probes alone was calculated by subtracting the average No DNA values from the probe values because it subtracted the contributions from contaminating ATP from the probe values. Thus, the formula used to determine the net light production from the reactions was:

Net Light=Total light−[(target alone)+(probe alone−no DNA)]

These data again indicate that improved allele detection results can be obtained by optimizing the amount of enzyme in the reaction. In addition, the results indicate that, while reading samples on a commercially available plate luminometer with automated reagent addition does not give the same readings as another instrument, the ratio of the relative signal strengths from reactions performed with matched and mismatched probes are approximately equal. Thus, automated reading of the reaction products can be used to perform allele determination.

FV1

5'CTAATCTGTAAGAGCAGATCCCTGGACAGGCGAGGAATACAGAGGGCAGCA    SEQ ID NO:10

GACATCGAAGAGCT 3'

FV2

5'AGCTCTTCGATGTCTGCTGCCCTCTGTATTCCTCGCCTGTCCAGGGATCTG    SEQ ID NO:11

CTCTTACAGATTAGAGCT 3'

FV5 5'CTGCTGCCCTCTGTATTCCTCG 3'    SEQ ID NO:12

FV6 5'CTGCTGCCCTCTGTATTCCTTG 3'    SEQ ID NO:13

EXAMPLE 5

The Effects of Enzyme Reduction on Allele Discrimination

Allele discrimination is further improved in this example by further reduction in the amount of enzyme used in the pyrophosphorylation reaction. Oligonucleotides CM1 (SEQ ID NO:9), CM2 (SEQ ID NO:8) and CM3 (SEQ ID NO:7) were dissolved in water, and CM1 was then diluted to 0.3 μg/mL in water. These reagents were used to form the following solutions.

| Solution | CM1 (μL) | CM2 (μL) | CM3 (μL) | Water (μL) |
|---|---|---|---|---|
| #1 | 1 | 1 | — | 18 |
| #2 | 1 | — | 1 | 18 |
| #3 | 1 | — | — | 19 |
| #4 | — | 1 | — | 19 |
| #5 | — | — | 1 | 19 |
| #6 | — | — | — | 20 |

These solutions were heated to 91° C. for 7 minutes, then permitted to cool for 15 minutes at room temperature. A master mix was assembled as in Example 4 except that the volumes used permitted 5–390 μL samples of the final mix to be placed into 5 0.5 mL microfuge tubes.

Klenow Exo- was diluted as described in Example 3 except the dilutions were adjusted so the diluted solutions contained 20, 10, 5, and 2.5 units of enzyme per 10 μL of diluted material. Ten microliters of the diluted enzyme solutions were added to four tubes containing 390 μL of master mix. Ten microliters of 1×DNA polymerase buffer (made by 1:10 dilution of 10×DNA Polymerase buffer with water) were added to a fifth tube with master mix to serve as a no-enzyme control. Twenty microliters of each of the master mixes and control mix were added to groups of three of solutions 1–6 above and each resulting solution was heated at 37° C. for 15 minutes, then the tube was placed on ice. After all tubes were processed in this manner, 5 μL samples from each of the tubes were separately added to 100 μL of L/L reagent (Promega, F202A) and the light produced by the solution immediately read using a Turner® TD 20/20 luminometer. The results for the triplicate determinations were averaged and those averages are presented in the table below.

Relative Light Units Measured in
Reactions at Various Enzyme Levels (enz/rx)

| Reaction Type | 2 U enz/rx | 1 U enz/rx | 0.5 U enz/rx | 0.25 U enz/rx | no enz |
|---|---|---|---|---|---|
| Matching probe | 279.0 | 301.3 | 306.6 | 268.3 | 3.94 |
| Mismatched probe | 24.51 | 23.95 | 25.02 | 13.70 | 4.35 |
| CM1 alone | 4.33 | 4.55 | 4.75 | 4.42 | 3.71 |
| CM2 alone | 3.90 | 4.05 | 3.91 | 4.44 | 3.75 |
| CM3 alone | 7.06 | 5.06 | 4.13 | 4.57 | 3.93 |
| No DNA | 3.35 | 3.52 | 4.01 | 3.94 | 3.27 |
| Ratio* | 16.6 | 16.6 | 15.0 | 30.4 | (nd) |

*Ratio determined by taking the net relative light units as described in Example 4 for the matching and mismatched primers and dividing the matching probe value by the mismatched probe value.

These data show that a very large degree of allele discrimination can be obtained by lowering the Klenow Exo- level to 0.25 U/reaction.

| | | |
|---|---|---|
| CM1 5' GCAACGCTACCTTTGCCATGTTTG 3' | | SEQ ID NO:9 |
| CM2 5' CACTTTGATATTACACCCGTG 3' | | SEQ ID NO:8 |
| CM3 5' CACTTTGATATTACACCCATG 3' | | SEQ ID NO:7 |

EXAMPLE 6

Reduction of Background Light Production by Reduction of Enzyme Concentrations A method to reduce the signal production from probes is demonstrated in this example. Thus, probes PH1 (SEQ ID NO:14), PH2 (SEQ ID NO:15), PH3 (SEQ ID NO:16), and PH4 (SEQ ID NO:17) were dissolved in water to a concentration of 1 mg/mL. The following solutions were assembled in duplicate.

| Solution | PH Probe (μL) | Water (μL) |
|---|---|---|
| #1 | — | 20 |
| #2 | 1, PH1 | 19 |
| #3 | 1, PH2 | 19 |
| #4 | 1, PH3 | 19 |
| #5 | 1, PH4 | 19 |

The solutions were heated at 95° C. for 5 minutes then cooled at room temperature for 10 minutes. The following two master mixes were assembled.

| Component | 0.25 U Master Mix (μL) | 5.0 U Master Mix (μL) |
|---|---|---|
| 10 X DNA Polymerase Buffer | 20 | 20 |
| Klenow Exo- (1 U/μL)* | 1.25 | — |
| Klenow exo- (10 U/μL) | — | 2.5 |
| 40 mM Sodium Pyrophosphate | 2.5 | 2.5 |
| NDPK (1 U/μL) | 1 | 1 |
| ADP (10 μM, Sigma) | 2 | 2 |
| Water | 73.25 | 72 |
| | 100 | 100 |

*Made by a 1:10 dilution of Klenow exo- with 1 X DNA polymerase buffer (1 X DNA Polymerase buffer made by 1:10 dilution of 10 X DNA Polymerase Buffer).

These master mixes were mixed and 20 μL of each master mix were added to one of each of solutions 1–5 above and heated at 37° C. for 15 minutes. Duplicate four microliter samples of each solution containing DNA were added to 10 μL L/L reagent (Promega F202A) and the light produced was immediately read using a Turner® TD 20/20 luminometer. A single 4 μL sample of the reactions not containing DNA was also read by adding it to 100 μl of L/L reagent and reading as above. The following results were obtained.

Relative Light Units

| Solution | 0.25 U Master Mix Reactions* | | | 5.0 U Master Mix Reactions* | | |
|---|---|---|---|---|---|---|
| | 1st. | 2nd. | Avg. | 1st. | 2nd. | Avg. |
| #1 (no DNA) | 6.89 | | | 7.32 | | |
| #2 (PH1) | 6.82 | 6.36 | 6.60 | 8.42 | 8.63 | 8.50 |
| #3 (PH2) | 17.38 | 14.25 | 15.8 | 195.1 | 185.8 | 190.3 |
| #4 (PH3) | 20.4 | 20.4 | 20.4 | 256.6 | 381.0 | 318.8 |
| #5 (PH4) | 8.35 | 7.56 | 7.96 | 20.24 | 32.68 | 26.5 |

*Data are from a first (1st.) and second (2nd.) reading that are averaged (Avg.).

These data indicate that probes PH2 and PH3 produce very high probe-alone light signals when a master mix containing 5U of Klenow exo-/reaction was used, and produced a greatly reduced light signal when 0.25 U of Klenow exo-/reaction was used. Thus, some probes that produce very high light values with one enzyme concentration can be useful in allele determination reactions if used in reactions with a lowered amount of enzyme.

PH1  5'CTGAACATGCCTGCCAAAGACG 3'    SEQ ID NO:14

PH2  5'CTGAACATGCCTGCCAAAGATG 3'    SEQ ID NO:15

PH3  5'CAGGAACGTAGGTCGGACACGT 3'    SEQ ID NO:16

PH4  5'CAGGAACGTAGGTCGGACACAT 3'    SEQ ID NO:17

EXAMPLE 7

Reduction of Probe-alone Background Values for Probes Designed to Interrogate a Viral Sequence In this Example, the background light values from probe-alone reactions are reduced by alteration of reaction conditions. More specifically, the values from such background reactions are reduced by lowering the Klenow exo-level in the reactions as shown in Example 6. In addition, the probes are used to assay the relative probe signal strength values for probes that hybridize to the same DNA strand versus probes that hybridize to different strands but that interrogate the same nucleotide polymorphism site.

Oligonucleotides CV11 (SEQ ID NO:18) and CV12 (SEQ ID NO:19) are a pair of single-stranded DNAs that can hybridize together to produce a segment of the genome of cytomegalovirus (CMV) in a form sensitive to the drug gancyclovir. Oligonucleotides CV13 (SEQ ID NO:20) and CV14 (SEQ ID NO:21) are a pair of single-stranded DNAs that can hybridize together to produce the same segment of the CMV genome, but differ from CV11 and CV12 in that they contain a SNP that represents a form of the virus resistant to the drug gancyclovir.

Probe oligonucleotide CV15 (SEQ ID NO:22) can hybridize with exact homology to a segment of CV12. Probe oligonucleotide CV16 (SEQ ID NO:23) is identical to CV15 except that it contains a one base change from the CV15 sequence at the site of the SNP that confers drug resistance to the virus. Probe oligonucleotide CV17 (SEQ ID NO:24) can hybridize with exact homology to CV11. Probe oligonucleotide CV18 (SEQ ID NO:25) is identical to CV17 except that it contains a one base change from the CV17 sequence at the site of the SNP that confers drug resistance to the virus.

The oligonucleotides above were dissolved in water at a concentration of 1 mg/mL and the following solutions were assembled.

| Solution | Oligonucleotide | Water |
|---|---|---|
| #1 | — | 20 µL |
| #2 | CV15, 1 µL | 19 µL |
| #3 | CV16, 1 µL | 19 µL |
| #4 | CV17, 1 µL | 19 µL |
| #5 | CV18, 1 µL | 19 µL |

These solutions were heated at 95° C. for 5 minutes, then cooled at room temperature for 10 minutes. A master mix was prepared as in Example 1 containing Klenow exo- at a concentration of 0.25 U/20 µL of solution. Twenty microliters of this solution were added to solutions 1–5 above after they had cooled, and then the resulting mixtures were heated at 37° C. for 15 minutes. After this incubation, 4 µL of each solution were added to 100 µL of L/L reagent (Promega F202A) and the light production of the resulting solution was measured immediately using a Turner® TD 20/20 luminometer. The following results were obtained.

| Solution sampled | Relative light units |
|---|---|
| #1 | 13.07 |
| #2 | 14.98 |
| #3 | 14.27 |
| #4 | 28.25 |
| #5 | 583.70 |

These results demonstrate that probes CV15–CV17 provide relatively low probe-alone light signals at 0.25 U Klenow exo- per reaction but that probe CV18-alone provides a very high relative light signal. The sequence of the CV18 probe can form a hairpin structure such that the terminal 3' bases hybridize to the sequence 5'TCGTGC 3' further towards the 5' end of the segment. Although probe CV17 could form the same structure, the terminal 3' base of the resulting structure would have a mispaired base.

These data exemplify one of the guiding principles of appropriate probe design for this system: the probes should not be predicted to form stable hairpin structure and, in particular, should not be predicted to give such a structure with the 3' end of the probe producing a structure that forms a blunt end or 5' overhang in the fragment as they may act as a substrate for the depolymerizing enzyme. In addition, the probes used should not be predicted to form probe dimer structures with either blunt ends or 5' overhanging ends because such probes can produce high probe-alone signals in the system and might make them unacceptable for use.

Due to their low background, probes CV15–CV17 were then selected for further study. Equal volumes of oligonucleotides CV11 and CV12 were annealed together as described in Example 1, as were CV13 and 14. The annealed solutions of CV11 and CV12, and CV13 and CV14 were labeled CV11+12 and CV13+14, respectively. The following solutions were assembled.

| Solution | CV15 | CV16 | CV17 | CV11 + 12 | CV13 + 14 | CV(11 + 12) + (13 + 14) Heterozyg Template | Water |
|---|---|---|---|---|---|---|---|
| #1 | — | — | — | — | — | — | 20 μL |
| #2 | 1 μL | — | — | — | — | — | 19 μL |
| #3 | — | 1 μL | — | — | — | — | 19 μL |
| #4 | — | — | 1 μL | — | — | — | 19 μL |
| #5 | — | — | — | 1 μL | — | — | 19 μL |
| #6 | — | — | — | — | — | 1 μL | 19 μL |
| #7 | — | — | — | — | 1 μL | — | 19 μL |
| #8 | 1 μL | — | — | 1 μL | — | — | 18 μL |
| #9 | — | 1 μL | — | 1 μL | — | — | 18 μL |
| #10 | 1 μL | — | — | — | — | 1 μL | 18 μL |
| #11 | — | 1 μL | — | — | — | 1 μL | 19 μL |
| #12 | 1 μL | — | — | — | 1 μL | — | 18 μL |
| #13 | — | 1 μL | — | — | 1 μL | — | 18 μL |
| #14 | 1 μL | — | — | 1 μL | — | — | 18 μL |
| #15 | — | — | 1 μL | 1 μL | — | — | 18 μL |
| #16 | 1 μL | — | — | — | — | 1 μL | 18 μL |
| #17 | — | — | 1 μL | — | — | 1 μL | 18 μL |
| #18 | 1 μL | — | — | — | 1 μL | — | 18 μL |
| #19 | — | — | 1 μL | — | 1 μL | — | 18 μL |

These solutions were heated at 95° C. for 5 minutes and then permitted to cool for 10 minutes at room temperature. A master mix solution was assembled as in Example 1 containing Klenow exo- at a final concentration of 0.25 U/20 μL. After solutions 1–19 had cooled, 20 μL of the master mix solution were added and the resulting solution heated at 37° C. for 15 minutes. After this incubation, duplicate 4 μL samples of solutions 2–19 and a single sample of solution 1 were taken, added to 100 μL of L/L reagent (Promega, F202A) and the light production of the mixture measured immediately using a Turner® TD 20/20 luminometer. The following results were obtained.

| | Relative light units | |
|---|---|---|
| Solution | Reading 1 | Reading 2 |
| #1 | 10.53 | — |
| #2 | 11.35 | 12.16 |
| #3 | 10.79 | 12.75 |
| #4 | 17.70 | 16.76 |
| #5 | 12.78 | 11.12 |
| #6 | 11.36 | 11.48 |
| #7 | 12.38 | 12.16 |
| #8 | 348.3 | 369.3 |
| #9 | 73.11 | 74.48 |
| #10 | 289.5 | 283.6 |
| #11 | 509.8 | 364.0 |
| #12 | 120.2 | 108.6 |
| #13 | 785.4 | 595.7 |
| #14 | 764.3 | 763.3 |
| #15 | 77.25 | 73.22 |
| #16 | 530.9 | 541.2 |
| #17 | 476.1 | 419.6 |
| #18 | 339.4 | 262.7 |
| #19 | 943.2 | 964.0 |

The results from the readings above were averaged and the net light units calculated as described in Example 2. These values were used to calculate ratios also as described in Example 2. The results of these calculations are presented in the tables below, wherein "WT" indicates the wild type genotype.

| Probes Interrogate the Same DNA Strand | | | | Probes Interrogate Different DNA Strands | | | |
|---|---|---|---|---|---|---|---|
| | Template Genotype | | | | Template Genotype | | |
| Probe | C/C | C/T | T/T | Probe | C/C | C/T | T/T |
| WT Probe (CV15) | 345.5 | 274.0 | 100.8 | WT Probe (CV15) | 745.1 | 518.0 | 282.1 |
| Mutant Probe (CV16) | 60.5 | 424.3 | 677 | Mutant Probe (CV17) | 61.9 | 435.0 | 940 |
| Ratio | 5.7 | 1.5 | 0.15 | Ratio | 12 | 1.2 | 0.33 |

These data demonstrate that, for this particular SNP, probes that detect the polymorphism that bind to different strands provide the signal ratio closest to 1.0 when both nucleic acid targets are present in the reaction (as occurs for samples heterozygous for a particular allele). However, either set of probes gives clearly different signals depending upon the genotype of the sample DNA.

CV11

5'CGCTTCTACCACGAATGCTCGCAGACCATGCTGCACGAATACGTCAGAAAG    SEQ ID NO:18

AACGTGGAGCGTCTGTTGGAGCT 3'

-continued

CV12

5'CCAACAGACGCTCCACGTTCTTTCTGACGTATTCGTGCAGCATGGTCTGCG SEQ ID NO:19

AGCATTCGTGGTAGAAGCGAGCT 3'

CV13

5'CGCTTCTACCACGAATGCTCGCAGATCATGCTGCACGAATACGTCAGAAA SEQ ID NO:20

GAACGTGGAGCGTCTGTTGGAGCT 3'

CV14

5'CCAACAGACGCTCCACGTTCTTTCTGACGTATTCGTGCAGCATGATCTGCG SEQ ID NO:21

AGCATTCGTGGTAGAAGCGAGCT 3'

| CV15 | 5' CTACCACGAATGCTCGCAGAC 3' | SEQ ID NO:22 |
| CV16 | 5' CTACCACGAATGCTCGCAGAT 3' | SEQ ID NO:23 |
| CV17 | 5' TGACGTATTCGTGCAGCATGG 3' | SEQ ID NO:24 |
| CV18 | 5' TGACGTATTCGTGCAGCATGA 3' | SEQ ID NO:25 |

EXAMPLE 8

Enhancing Output Discrimination by Destabilizing Interrogation Probes with Internal Mismatches Prothrombin PCR fragments were interrogated to determine if they contained a single nucleotide polymorphism (SNP) mutation in the human prothrombin gene that is characterized by a G to A substitution in the prothrombin gene. The interrogation probes were designed to compare data when there is a potential for a mismatched nucleotide only at the 3'-terminal base of the interrogation probe versus an interrogation probe having this same potential mismatch and an additional mismatch 9 bases from the 3'end.

Probes PT5 and PT6 (SEQ ID NO:26 and SEQ ID NO:27, respectively) were used to PCR amplify a region of human genomic DNA spanning about 500 base pairs encoding the prothrombin gene. The PT5 probe has phosphothioate linkages between the first five bases at the 5' end. As described before, these linkages, present on one strand of the resulting PCR product, are resistant to cleavage with T7 Polymerase Exonuclease 6 (Exo 6). The PCR reaction was set up as follows:

| 10 μL | 10× PCR buffer |
| 6 μL | 25 mM MgCl₂ |
| 2 μL | 10 mM dNTP mixture (2.5 mM each dNTP) |
| 2 μL | 100 pmoles probe PT5 |
| 2 μL | 100 pmoles probe PT6 |
| 4 μL | human genomic DNA (Promega, G3041) |
| 75 μL | water |
| 2.5 units | Taq (Promega, M1861) |

The PCR cycling parameters were: 94° C., 2 minutes; (94° C., 30 seconds; 60° C., 1 minute; 70° C., 1 minutes)× 35; 70° C., 7 minutes; 4° C. soak. Ten microliters of the PCR reaction were run on a 1.5% agarose gel, ethidium bromide stained, and a band of correct size was visualized under UV light. To 25 μL of the PCR reaction were added 50 units of Exo 6, and the sample was incubated at 37° C. for 15 minutes.

The sample was then treated with Exo 6 as described before, and purified away from the free nucleotides using MagneSil™ paramagnetic particles (Promega, A1330) according to manufacturer's instructions. Four microliters of the 100 μL eluted DNA were interrogated with probes PT7 (SEQ ID NO:28), PT8 (SEQ ID NO:29), PT9 (SEQ ID NO:30), and PT10 (SEQ ID NO:31) in four separate reactions.

PT7 and PT9 differ only in the nucleotide present nine nucleotides from the 3' end. Probe PT7 has a base complementary to the wild type sequence nine bases from the 3' end, whereas probe PT9 has a mismatching base at that position. These two probes have a 3' terminal nucleotide that matches wild type prothrombin. PT8 and PT10 differ only in the nucleotide present nine nucleotides from the 3' end. Probe PT8 has a base complementary to the wild type sequence nine bases from the 3' end, whereas probe PT10 has a mismatching base at that position. These two probes have a 3'-terminal nucleotide that matches the mutant prothrombin, but is a mismatch with wild type.

The interrogation reactions were set up as follows: 4 μL target DNA were combined with 150 pmol of interrogation oligonucleotide probe (or none for control reaction) and water to a final volume of 20 μL. These samples were incubated at 95° C. for 3 minutes, followed by incubation at 37° C. for 10 minutes. Then 20 μL master mix were added, and the tube incubated at 37° C. for an additional 15 minutes. The master mix contains 71 μL water, 20 μL 10×DNA Pol buffer (Promega, M195A), 5 μL 40 mM NaPP$_i$, 2 μL 10 μM ADP, 1 unit NDPK, and 2 units Klenow exo- (Promega, M218A). Then, 100 μL of L/L reagent (Promega, FF2021) were added and the relative light units measured immediately in a Turner® TD20/20 luminometer. The control values from samples lacking an interrogation oligonucleotide were subtracted and the results are reported in the Table below.

| Reaction | Interrogation oligo | Relative Light Units |
| --- | --- | --- |
| 1. | PT7 | 1520 |
| 2. | PT8 | 495 |

| Reaction | Interrogation oligo | Relative Light Units |
|---|---|---|
| 3. | PT9 | 1724 |
| 4. | PT10 | 219 |

The results indicate that the additional mismatch, internally located in the interrogation probe, helped to increase the level of discrimination observed between wild type and mutant probes. When the internal mismatch was not present in the interrogation probes, there was 3.1-fold discrimination, whereas when the internal mismatch was present in the interrogation probes, there was 7.9-fold discrimination.

| | | |
|---|---|---|
| PT5 | 5' ATAGCACTGGGAGCATTGAGGC 3' | SEQ ID NO: 26 |
| PT6 | 5' GCACAGACGGCTGTTCTCTT 3' | SEQ ID NO: 27 |
| PT7 | 5' GTGACTCTCAGCG 3' | SEQ ID NO: 28 |
| PT8 | 5' GTGACTCTCAGCA 3' | SEQ ID NO: 29 |
| PT9 | 5' GTGATTCTCAGCG 3' | SEQ ID NO: 30 |
| PT10 | 5' GTGATTCTCAGCA 3' | SEQ ID NO: 31 |

EXAMPLE 9

Effect of Increasing Phosphorothioate Linkages in PCR Primers on T7 Gene 6 Exonuclease Digestion of PCR Products Prior to Interrogation Reaction This Example was designed to determine the number of phosphorothioate linkages that, when present at the 5' end of a PCR primer, are sufficient to protect the strand of the resulting PCR product hybrid containing that primer from being degraded by T7 Gene 6 exonuclease. Such protection results in elevated relative light unit (rlu) values over background values when the exonuclease-treated PCR product hybrid is interrogated for the presence or absence of a particular nucleotide by a process of the invention.

Six oligonucleotides were designed for use in this study as PCR primers. Those six oligonucleotides are listed below. An asterisk (*) represents a phosphorothioate linkage.

Six reactions were set up in which 20 ng of wild type rice genomic DNA was PCR amplified using oligonucleotide 10667 and one of the other 5 nucleotides listed below. The following solutions were assembled.

| Component | Volume (µL) |
|---|---|
| 10× DNA Polymerase buffer without MgCl$_2$ (Promega M190A) | 5 |
| 25 mM MgCl$_2$ (Promega A351A) | 3 |
| 10 mM dNTP mixture (Promega C114A) | 1 |
| Primer 10667 (50 pmole/µL) | 1 |
| Second primer (50 pmole/µL) | 1 |
| Rice genomic DNA (10 ng/µL) | 2 |
| Water | 37 |
| Taq DNA Polymerase (Promega M186A) | 1.25U |

These solutions were heated to 94° C. for two minutes, then subjected to the following temperature cycling program for 35 cycles: one-half minute, 94° C.; one minute, 60° C.; one minute, 70° C. A solution was thereafter held at 70° C. for seven minutes, then cooled to 4° C.

One set of the five samples was not treated with T7 gene 6 exonuclease (USB, E700254). One set of the five samples was treated with 25 units (0.5 µL) of T7 gene 6 exonuclease for 30 minutes at room temperature. A third set of the five samples was treated with 25 units (0.5 µL) of T7 gene 6 exonuclease for 30 minutes at 37° C. All of the samples (25 µL) were then purified using magnetic silica particles following the method, as described in Example 2.

Five microliters of the purified reactions were interrogated using the rice wild type oligonucleotide RS3 (SEQ ID NO: 5) and the light output of the reaction measured using a Turner® TD20/20 luminometer. The results are listed below:

| Phosphoro-thioate linkages | T7 Gene 6 exo-nuclease | Incubation Temperature | Relative Light Units Interrogation Oligo | |
|---|---|---|---|---|
| | | | Wild type | none |
| 0 | – | 37° C. | 684.3 | 577.5 |
| 1 | – | 37° C. | 791.2 | 644.4 |
| 2 | – | 37° C. | 845.8 | 620.7 |
| 3 | – | 37° C. | 825.7 | 648.2 |
| 4 | – | 37° C. | 777.0 | 595.1 |
| 0 | + | room temp | 479.9 | 95.57 |
| 1 | + | room temp | 472.4 | 75.47 |
| 2 | + | room temp | 690.6 | 83.50 |
| 3 | + | room temp | 529.1 | 183.2 |
| 4 | + | room temp | 721.5 | 152.9 |
| 0 | + | 37° C. | 424.7 | 123.6 |
| 1 | + | 37° C. | 297.6 | 94.6 |
| 2 | + | 37° C. | 694.3 | 189.4 |
| 3 | + | 37° C. | 687.2 | 172.6 |
| 4 | + | 37° C. | 1068 | 270.3 |

*Net light output is calculated by subtracting the probe alone and DNA alone values from that obtained with both components present.

At both room temperature and 37° C. incubation, a significant decrease in no interrogation (background) signal was seen using T7 gene 6 exonuclease. This unexpected observation was seen even when there were no phosphorothioate linkages present in the PCR primer. Inclusion of phosphorothioate linkages increased the wild type oligonucleotide interrogation signal. A significant increase in signal was observed when two or more phosphorothioate linkages were incorporated into a PCR primer and the resulting PCR product was treated with T7 gene 6 exonuclease prior to interrogation.

```
10667  5' TCTCAAGACACAAATAACTGCAG 3'        SEQ ID NO: 4

10668  5' CCCAACACCTTACAGAAATTAGC 3'        SEQ ID NO: 32

12140  5' C*CCAACACCTTACAGAAATTAGC 3'       SEQ ID NO: 32*

12141  5' C*C*CAACACCTTACAGAAATTAGC 3'      SEQ ID NO: 32*

12142  5' C*C*C*AACACCTTACAGAAATTAGC 3'     SEQ ID NQ: 32*

12143  5' C*C*C*A*ACACCTTACAGAAATTAGC 3'    SEQ ID NO: 32*

RS3    5'AGAACATCTGCAAGG 3'                 SEQ ID NO: 5
```
An asterisk (*) indicates the probe as having the same sequence as in SEQ ID NO: 32, yet having phosphorothioate linkages present.

EXAMPLE 10

Probes for Detection of THO 1 Alleles using Destabilizing Internal Mismatches Additional probes are used in this Example to demonstrate that the creation of additional mismatches between THO 1 allele targets and probes can result in the formation of probe/target combinations that provide strong signals with essentially one THO 1 allele.

Probes TR 9 (SEQ ID NO:35), TR10 (SEQ ID NO:36) and TR11 (SEQ ID NO:37) were dissolved at 1 mg/mL and assembled into reactions with target at 3 ng/reaction with allele 6 (SEQ ID NO:38), allele 7 (SEQ ID NO:39), and allele 8 (SEQ ID NO:40) of THO 1 and without any target as described in the Example above. These solutions were heated and cooled as in the previous Example. The resulting solutions were treated with master mix, incubated, added to L/L reagent (Promega, F202A) and the light produced measured as in the previous Example. The following results were obtained.

|        | Relative Light Units | | | |
|--------|------------|-------------|-------------|------|
| Target | Probe TR9  | Probe TR10  | Probe TR11  | none |
| Allele 6 | 59.74 | 35.86 | 75.78 | 8.96 |
| Allele 7 | 51.73 | 2.32  | 15.85 | 10.54 |
| Allele 8 | 58.58 | 25.37 | 33.67 | 9.85 |
| (none)   | 47.27 | 34.24 | 3.676 | (nd) |

The values for the probe alone and target alone reactions were subtracted from the values for the combined reactions and are shown in the table below.

|        | Relative Light Units | | |
|--------|-----------|------------|------------|
| Target | Probe TR9 | Probe TR10 | Probe TR11 |
| Allele 6 | 3.51  | −7.34  | 63.14 |
| Allele 7 | −6.08 | −22.46 | 1.63  |
| Allele 8 | 1.46  | −18.72 | 20.14 |

Increasing the number of mismatched bases between the probe and target lowers the signal value measured, and in many cases decreases the values seen below those attributable from background reactions. In particular, probes TR9, which has a mismatch of 2 base pairs, and TR10, which has an A to C mutation 3 bases from the end of the probe, do not exhibit the ability to detect THO 1 alleles. However, probe TR11, which has a A to G change 3 bases from the end of the probe, produced a measurable signal with the allele 6 target that is greater than the signals seen with the other targets.

Probes TR12 (SEQ ID NO:73) and TR13 (SEQ ID NO:74) were then used as above. The following data were obtained.

|        | Relative Light Units | |
|--------|------------|------------|
| Target | Probe TR12 | Probe TR13 |
| Allele 6 | 9.7  | 9.8  |
| Allele 7 | 5.0  | 7.1  |
| Allele 8 | 10.4 | 12.6 |
| (none)   | 3.0  | 2.9  |

These probes, having additional mismatches four base pairs from the 3' end of the probe, only provided very low light signals and apparently did not discriminate between the alleles of THO 1. Thus, these data suggest that probes that can provide allele-specific signals can be identified by designing probes with base pair mismatches placed in the probe sequence near the 3' end of the probe.

Allele 6

5'GGTGAATGAATGAATGAATGAATGAATGAGGGAAATAAGGGAGGAAGAGGC  SEQ ID NO:38

CAATGGG 3'

Allele 7

5'GGTGAATGAATGAATGAATGAATGAATGAATGAGGGAAATAAGGGAGGAAG  SEQ ID NO:39

AGGCCAATGGG 3'

Allele 8

5'GGTAGGTGAATGAATGAATGAATGAATGAATGAATGAATGAGGGAAATAAG  SEQ ID NO:40

GGAGGAAGAGGCCAATGGG 3'

TR9

5' CCCATTGGCCTGTTCCTCCCTTATTTCCCTCATTCATTCATT  SEQ ID NO:35

CATTCATTCATTCAGC 3'

TR10

5' CCCATTGGCCTGTTCCTCCCTTATTTCCCTCATTCATTCATT  SEQ ID NO:36

CATTCATTCATTCCCC 3'

TR11

5' CCCATTGGCCTGTTCCTCCCTTATTTCCCTCATTCATTCATT  SEQ ID NO:37

CATTCATTCATTCGCC 3'

TR12

5' CCCATTGGCCTGTTCCTCCCTTATTTCCCTCATTCATTCATT  SEQ ID NO:73

CATTCATTCATTGACC 3'

TR13

5' CCCATTGGCCTGTTCCTCCCTTATTTCCCTCATTCATTCATT  SEQ ID NO:74

CATTCATTCATTAACC 3'

EXAMPLE 11

PRPP Synthetase, Reactions with Deoxyadenosine Monophosphate

Some schemes for the detection of DNA require the conversion of DAMP, generated by nuclease digestion of DNA, to DATP. This example demonstrates that the enzyme PRPP synthetase can perform the transformation of dAMP to DATP using PRPP as a co-substrate. In addition, this transformation can be monitored by luciferase detection at much higher sensitivities if the DATP formed is used to transform ADP to ATP through the action of NDPK added to the reaction.

The reactions were assembled in duplicate. The concentrations of the reaction components were as follows: $2.9 \times 10^{-4}$ M dAMP in 10 mM Tris pH 7.3; $2.9 \times 10^{-4}$ M AMP in 10 mM Tris pH 7.3; $2.6 \times 10^{-4}$ M PRPP in 10 mM Tris pH 7.3; 100×dilution of PRPP Syn (PRPP synthetase) (Sigma #P0287) stock enzyme which is at 0.03 U/$\mu$L. The components were added to twenty microliters of PRPP Synthetase Buffer (50 mM triethanolamine, 50 mM potassium phosphate, pH 7, 0.37 mM EDTA, 10 mM $MgCl_2$, 1 mg/mL BSA). After incubating for 47 minutes at 37° C., 100 $\mu$L LAR Buffer were added to all reactions along with 10 ng luciferase and the light output of the reactions was immediately measured. The data are presented in Relative Light Unit table below. PRPP was able to utilize dAMP as a substrate (comparing reaction 1 to 2, 3, 4 and 5). However, the amount of light produced by reaction was low, probably due to the fact that luciferase uses DATP at a much lower efficiency than ATP.

| Reaction | dAMP | PRPP | PRPP Syn |
|---|---|---|---|
| 1 | 2 $\mu$L | 2 $\mu$L | 2 $\mu$L |
| 2 | 2 $\mu$L | — | 2 $\mu$L |
| 3 | 2 $\mu$L | 2 $\mu$L | — |
| 4 | 2 $\mu$L | — | — |
| 5 | — | 2 $\mu$L | 2 $\mu$L |

| | Relative Light Unit | | |
|---|---|---|---|
| Reaction | Tube A | Tube B | Avg. Light |
| 1 | 18.2 | 22.1 | 20.15 |
| 2 | 1.4 | 1.4 | 1.4 |
| 3 | 4.2 | 3.8 | 4 |
| 4 | 2.1 | 1.8 | 1.95 |
| 5 | 13.1 | 15.8 | 14.45 |

In order to demonstrate the transfer of phosphate from DATP to ADP to form ATP, the reactions, as shown below, were assembled in duplicate in twenty microliters of PRPP Synthetase Buffer (above). They were then incubated at 37° C. for 34 minutes. The added components had the following formulations: $2.3 \times 10^{-2}$ M ADP in 10 mM Tris-Cl pH 7.3; 1000×dilution of NDPK (Sigma #N0379) at 10 U/$\mu$L (final concentration 0.01 U/$\mu$L). The tubes were then incubated for an additional 60 minutes at 37° C., 10 ng luciferase added, and the light output measured using a Turner® TD-20e Luminometer. The data are presented in the table below. These data indicate that the dATP produced by the PRPP Synthetase reaction can be transferred to ADP by the action of NDPK to produce ATP.

| | | Reactions Assembled | | | |
|---|---|---|---|---|---|
| Reaction | dAMP | PRPP | PRPP Syn | ADP | NDPK |
| 1 | 2 $\mu$L | 2 $\mu$L | 2 $\mu$L | 2 $\mu$L | 2 $\mu$L |
| 2 | 2 $\mu$L | 2 $\mu$L | 2 $\mu$L | — | — |
| 3 | 2 $\mu$L | 2 $\mu$L | 2 $\mu$L | 2 $\mu$L | — |
| 4 | 2 $\mu$L | 2 $\mu$L | 2 $\mu$L | — | 2 $\mu$L |
| 5 | — | 2 $\mu$L | 2 $\mu$L | 2 $\mu$L | 2 $\mu$L |

| | Light Units | |
|---|---|---|
| Reaction | Tube A | Tube B |
| 1 | 812.1 | 839.3 |
| 2 | 19.2 | 37.5 |
| 3 | 53.6 | 52.6 |
| 4 | 168.4 | 173.1 |
| 5 | 43.6 | 38.9 |

EXAMPLE 12

Detection of PhiX 174 HinF1 Fragments Using Nucleases, PRPP Synthetase, NDPK This example demonstrates the detection of DNA by digestion of the polymer to nucleoside monophosphates using nucleases, transformation of the nucleoside monophosphates to nucleoside triphosphates using PRPP Synthetase and PRPP along with transformation of ADP to ATP using the nucleoside triphosphates generated by the action of PRPP Synthetase, and detection of the ATP using luciferase. A sample of deoxynucleotide (Poly (dA)) was prepared as described in Example 85. Different amounts of deoxynucleotide were used in the reactions as presented in Table 30.

The following additions were made to each reaction: 2 $\mu$L PRPP, 2 $\mu$L PRPP Synthetase, and 20 $\mu$L PRPP Synthetase buffer. The reactions proceeded at 37° C. for 28 minutes, at which time the reactions were transferred to 100 $\mu$l LAR Buffer containing 2 $\mu$L ADP and 2 $\mu$L NDPK. This second reaction was permitted to proceed at room temperature for 20 minutes. The amount of ATP produced was measured by the addition of 10 ng of luciferase followed by measuring light output with a luminometer. The data are presented in table below. These data show that this combination of enzymes permitted detection of DNA.

| Reaction | Nucleotide | Amount In Reaction | Light Units |
|---|---|---|---|
| 1 | dAMP | 200 ng, 600 pmoles | 1018 |
| 2 | dAMP | 20 ng, 60 pmoles | 636 |
| 3 | dAMP | 2 ng, 6 pmoles | 178 |
| 4 | dAMP | 200 pg, 600 fmoles | 83 |
| 5 | none | zero ng | 69 |

-continued

| Reaction | Nucleotide | Amount In Reaction | Light Units |
|---|---|---|---|
| 6 | PhiX 174 only | 100 ng (= 300 pmoles dNMP; about 75 pmoles dAMP) | 46 |
| 7 | PhiX 174 + ExoIII | 100 ng | 472 |
| 8 | PhiX 174 + Exo + S1 | 100 ng | 448 |
| 9 | No DNA + Exo + S1 | zero ng | 55 |

EXAMPLE 13

Tne Triple Mutant Tne Polymerase and Thermostable NDPK Used to Interrogate Congenital Adrenal Hyperplasia Congenital adrenal hyperplasia (CAH) is a group of autosomal recessive diseases resulting from a wide range of mutations in the steroid 21-hydroxylase (CYP21) gene that contains 10 exons. There is a high level of nucleic acid homology (98% in exons, 96% in introns) between CYP21, the functional gene, and CYP21P, the nonfunctional pseudogene. The many types of mutations in this gene that can lead to disease include complete gene deletions, large gene conversions, single point mutations, and a small 8 bp deletion [See, White, et al., Hum. Mutat., 3:373–378, (1994)].

The majority of the CAH disease-causing mutations are sequences present in the nonexpressed CYP21P pseudogene, and arise in the CYP21 gene through recombination between CYP21P and CYP21. Thus, one mutation detection strategy specifically detects the CYP21 gene, and not the CYP21P pseudogene. The frequency of disease-carrying alleles in the population is about 1 in 50.

In this Example, the CAH target was interrogated for a variety of mutations using Klenow exo- and yeast NDPK, and the results were compared to a similar analysis using Tne triple mutant thermostable DNA polymerase and a thermostable Pfu NDPK. Both wild type CAH PCR products, mutant synthetic targets, and a pseudogene PCR product amplified from the cloned CYP21P pseudogene were utilized as targets in this assay. They are listed below.

Primer pairs used in PCR amplification and the resulting products are as follows.

| Primers | Size PCR Segment | Segment Amplified |
|---|---|---|
| 10912 + 10909 | 1400 bp | 5' end CYP21 |
| 11461 + 11480 | 918 bp | 5' end CYP21 |
| 10910 + 11286 | 1492 bp | 3' end CYP21 |
| 11535 + 11286 | 1496 bp | 3' end CYP21 |
| 10912 + 10911 | 2680 bp | pseudogene (CYP21P) |

Synthetic targets and interrogation oligos utilized are listed below.

PCR reactions were assembled to amplify regions of the CAH gene with 4 different probe sets, using undigested human genomic DNA (Promega, G3041) as target (25 ng per reaction). For amplification of the pseudogene, human genomic DNA was predigested with the restriction enzyme Bcl I, which specifically cleaves the CYP21 gene upstream of the forward PCR probe, thus permitting only amplification of CYP21P [Krone, *Clinical Chem.* 44(10):2075–2082 (1998)].

The 2680 bp PCR product was amplified from 50 ng of digested DNA and subsequently cloned into the plasmid vector pGEM-T Easy (Promega, A1380) following the manufacturer's protocol. A clone was selected and sequenced (USB Sequenase kit, US70770) to confirm it was indeed the pseudogene. The cloned CYP21P gene in the pGEM-T Easy vector was used in subsequent amplifications to obtain pure pseudogene PCR product for mutation interrogation analysis (100 pg of plasmid per PCR reaction).

All 50 μL amplification reactions contained the following reagents: genomic DNA (as described above), 1×reaction buffer (M1901), 1.0–1.5 mM magnesium chloride (all with 1.0 mM except probe pair 10912+10911 for pseudogene, which contained 1.5 mM MgCl$_2$; Promega, A3511), 200 μM each DNTP (C1141), 50 pmoles each probe, and 2.5 units Taq DNA Polymerase (M1665).

The following cycling profile was utilized for all amplifications: 5 minutes at 95° C.; 40 cycles of 30 seconds at 94° C., 1 minute at 55° C., 1 minute per kbp of product at 72° C.; 8 minutes at 68° C.; soak at 4° C. The products were analyzed on 1% agarose gels and compared to DNA molecular weight standards to confirm product sizes were correct. An aliquot of each PCR reaction (25 μL) was then treated with 50 units T7 Gene6 Exonuclease (USB, E70025Y) for 15 minutes at 37° C., followed by purification using the Wizard™ PCR Prep DNA Purification System (Promega, A7170) with 3×1 mL 80% isopropanol washes. The exonuclease-treated DNA was eluted in 100 μL of nuclease-free water.

Each interrogation assay (20 μL total volume) contained 4 μL of purified PCR product or 5 ng of synthetic target, and 1 μg interrogation oligo probe (or water for the no-oligo background control). The reactions were incubated at 95° C. for 3 minutes, followed by 10 minutes at 37° C. for Klenow exo- or 55° C. for Tne polymerase. Twenty microliters of master mix were added (2 mM sodium pyrophosphate, 0.2 μM ADP, 2×polymerase buffer (M195A for Klenow or M1901 for Tne), 5 mM magnesium chloride for Tne only, 1–2 U Klenow exo- and 0.2 U yeast NDPK or 1 U Tne triple mutant polymerase and 0.1 U Pfu NDPK) and the reaction incubated 15 minutes at 37° C. (Klenow exo-) or 55° C. (Tne). The entire reaction was then added to 100 μL of L/L reagent (Promega FF202A) and light output read in a Turner® TD20/20 luminometer.

Although 55° C. was used in these studies with the Tne triple mutant polymerase and the Pfu NDPK, higher temperatures can also be used. The 55° C. temperature selected appeared to be a good compromise between interrogation oligo annealing and enzymatic activity. Thus, higher incubation temperatures can be beneficial if longer interrogation oligos are utilized.

The table below contains the relative light units (rlu) obtained. The data represent the combined results of many separate studies using the various enzymes. The use of the Tne triple mutant polymerase and Pfu NDPK particularly improved the discrimination ratio for the CAH wild type PCR products at mutation sites 2 and 6, whereas the thermostable enzymes improved the discrimination ratio for the mutant pseudogene PCR product at mutation sites 3, 4, and 5. The synthetic targets worked well with both enzymes, however the signals and discrimination ratios were higher for the thermostable enzymes at almost all of the mutation sites.

| Target DNA | Klenow/ NDPK No oligo | Klenow/ NDPK WT oligo | Klenow/ NDPK Mutant oligo | Tne/ Pfu NDPK No oligo | Tne/ Pfu NDPK WT* oligo | Tne/ Pfu NDPK Mutant oligo | Mut* Site |
|---|---|---|---|---|---|---|---|
| CAH WT 1400 bp | 176.9 | 1050.0 | 204.0 | | | | 1 |
| CAH WT 1400 bp | 176.9 | 1149 | 625.5 | | | | 2 |
| CAH WT 1492 bp | 388.9 | 496.2 | 414.7 | | | | 3 |
| CAH WT 1492 bp | 388.9 | 881.4 | 383.9 | | | | 4 |
| CAH WT 1492 bp | 388.9 | 940.3 | 477.3 | | | | 5 |
| CAH WT 1492 bp | 388.9 | 205.2 | 207.0 | | | | 6 |
| CAH WT 918 bp | | | | 129.4 | 443.0 | 125.6 | 1 |
| CAH WT 918 bp | | | | 129.4 | 440.9 | 134.7 | 2 |
| CAH WT 1496 bp | | | | 124.3 | 261.6 | 118.3 | 3 |
| CAH WT 1496 bp | | | | 124.3 | 259.4 | 121.7 | 4 |

-continued

| | Klenow/ NDPK | Klenow/ NDPK | Klenow/ NDPK | Tne/ Pfu NDPK | Tne/ Pfu NDPK | Tne/ Pfu NDPK | |
|---|---|---|---|---|---|---|---|
| CAH WT 1496 bp | | | | 124.3 | 276.3 | 135.6 | 5 |
| CAH WT 1496 bp | | | | 124.3 | 214.0 | 112.3 | 6 |
| CAH WT 1496 bp | | | | 124.3 | 252.5 | 174.5 | 7 |
| Pseudo -gene 2680 bp | 15.89 | 115.7 | 109.2 | 176.1 | 419.0 | 537.3 | 1 |
| Pseudo -gene 2680 bp | 15.89 | 45.29 | 140.4 | 176.1 | 388.6 | 397.5 | 2 |
| Pseudo -gene 2680 bp | 15.89 | 129.6 | 141.6 | 176.1 | 477.8 | 772.5 | 3 |
| Pseudo -gene 2680 bp | 15.89 | 63.34 | 149.2 | 176.1 | 369.4 | 999.7 | 4 |
| Pseudo -gene 2680 bp | 15.89 | 115.8 | 91.28 | 1676.1 | 412.1 | 945.9 | 5 |
| Pseudo -gene 2680 bp | | | | 176.1 | 202.7 | 945.0 | 7 |
| Syn- thetic Temp. 1 | 95.65 | 128.2 | 831.2 | 56.92 | 76.58 | 1499 | 1 |
| Syn- thetic Temp. 2 | 81.09 | 119.3 | 774.9 | 58.46 | 171.8 | 1521 | 2 |
| Syn- thetic Temp. 3 | 83.22 | 315.6 | 1496 | 54.05 | 171.2 | 2206 | 3 |
| Syn- thetic Temp. 4 | 87.71 | 85.82 | 1199 | 55.29 | 152.1 | 2829 | 4 |
| Syn- thetic Temp. 5 | 78.80 | 332.5 | 1071 | 57.49 | 76.91 | 837.7 | 5 |
| Syn- thetic Temp. 6 | 79.86 | 57.0 | 322.0 | 56.68 | 140.6 | 2328 | 6 |
| Syn- thetic Temp. 7 | 86.99 | 1738 | 1285 | 209.2 | 4162 | 351.3 | 2 |
| Syn- thetic Temp. 8 | 98.50 | 1005 | 29.24 | 212.2 | 2121 | 260.4 | 6 |

*WT = wild type; Mut = mutation; Temp. = template

PCR PRIMERS UTILIZED:

10909   5' CCAGAGCAGGGAGTAGTCTC 3'          SEQ ID NO:41

CAH reverse primer; 5' most 3 linkages phosphorothioate (CYP21 only)

10912   5' GCATATAGAGCATGGCTGTG 3'          SEQ ID NO:42

CAH forward primer

-continued

```
10910    5' CCTGTCCTTGGGAGACTAC 3'              SEQ ID NO:43
CAH forward primer (CYP21 only)

10911    5' CCCAGTTCGTGGTCTAGC 3'               SEQ ID NO:44
CAH reverse primer; 5' most 3 linkages
phosphorothioate 11286    5' TCCTCACTCATCCCCAAC 3'               SEQ ID NO:45
CAH reverse primer; 5' most 3 linkages
phosphorothioate 11461    5'GAAATACGGACGTCCCAAGGC 3'             SEQ ID NO:46
CAH forward primer 11480    5'CTTTCCAGAGCAGGGAGTAG                 SEQ ID NO:47
CAH reverse primer; 5' most 3 linkages
phosphorothioate (CYP21 only)

11535    5'CCGGACCTGTCCTTGGGAGA                 SEQ ID NO:48
CAH forward primer (CYP21 only)

SYNTHETIC TARGETS UTILIZED:

11293  5' AGAAGCCCGGGGCAAGAGGCAGGAGGTGGAGGCTCCGGAG 3'   SEQ ID NO:49
       CAH Synthetic Target 1 for Interrogator oligo 1
(pseudogene/mutant - exon 1)
       Mutation site 1

11294  5' AGCTTGTCTGCAGGAGGAGCTGGGGGCTGGAGGGTGGGAA 3'   SEQ ID NO:50
       CAH Synthetic Target 2 for Interrogator oligo 2
(pseudogene/mutant - intron 2)
            Mutation site 2

11295  5' TCCGAAGGTGAGGTAACAGTTGATGCTGCAGGTGAGGAGA 3'   SEQ ID NO:51
       CAH Synthetic Target 3 for Interrogator oligo 3
(pseudogene/mutant - exon 4)
       Mutation site 3

11296  5' TCCACTGCAGCCATGTGCAAGTGCCCTTCCAGGAGCTGTC 3'   SEQ ID NO:52
       CAH Synthetic Target 4 for Interrogator oligo 4
(pseudogene/mutant - exon 7)
       Mutation site 4

11297  5' TCGTGGTCTAGCTCCTCCTACAGTCGCTGCTGAATCTGGG 3'   SEQ ID NO:53
       CAH Synthetic Target 5 for Interrogator oligo 5
(pseudogene/mutant - exon 8)
       Mutation site 5

11298  5' GCTAAGGGCACAACGGGCCACAGGCGCAGCACCTCGGCGA 3'   SEQ ID NO:54
       CAH Synthetic Target 6 for Interrogator oligo 12
(pseudogene/mutant - exon 8)
       Mutation site 6
```

-continued

```
11484  5'CAGCTTGTCTGCAGGAGGAGTTGGGGGCTGGAGGGTGGGA 3'   SEQ ID NO:55
    CAH Synthetic Target 7 for Interrogator oligo 7
(wild type - intron 2)
    Mutation site 2
11485  5'GGCTAAGGGCACAACGGGCCGCAGGCGCAGCACCTCGGCG 3'   SEQ ID NO:56
    CAH Synthetic Target 8 for Interrogator oligo 11
(wild type - exon 8)
    Mutation site 6
INTERROGATION OLIGOS PROBES UTILIZED:
11143     5' CGGAGCCTCCACCTCCCG 3'              SEQ ID NO:57
CAH interrogator oligo 6 (wild type) for mutation
site 1
11085     5' CACCCTCCAGCCCCCAGC 3'              SEQ ID NO:58
CAH interrogator oligo 2 (pseudogene/mutant) for
mutation site 2
11084     5' CGGAGCCTCCACCTCCTG 3'              SEQ ID NO:59
CAH interrogator oligo 1 (pseudogene/mutant) for
mutation site 1
11086     5' CCTCACCTGCAGCATCAAC 3'             SEQ ID NO:60
CAH interrogator oligo 3 (pseudogene/mutant) for
mutation site 3
11144     5' CACCCTCCAGCCCCCAAC 3'              SEQ ID NO:61
CAH interrogator oligo 7 (wild type) for mutation
site 2
11145     5' CCTCACCTGCAGCATCATC 3'             SEQ ID NO:62
CAH interrogator oligo 8 (wild type) for mutation
site 3
11087     5' CCTGGAAGGGCACTT 3'                 SEQ ID NO:63
CAH interrogator oligo 4 (pseudogene/mutant) for
mutation site 4
11146     5' CCTGGAAGGGCACGT 3'                 SEQ ID NO:64
CAH interrogator oligo 9 (wild type) for mutation
site 4
11088     5' GATTCAGCAGCGACTGTA 3'              SEQ ID NO:65
CAH interrogator oligo 5 (pseudogene/mutant) for
mutation site 5
11147     5' GATTCAGCAGCGACTGCA 3'              SEQ ID NO:66
CAH interrogator oligo 10 (wild type) for mutation
site 5
11287     5' CGAGGTGCTGCGCCTGCG 3'              SEQ ID NO:67
```

-continued

CAH interrogation oligo 11 (wild type) for mutation site 6

11288    5'CGAGGTGCTGCGCCTGTG 3'                SEQ ID NO:68

CAH interrogation oligo 12 (pseudogene/mutant) for mutation site 6

11641    5'GGGATCACATCGTGGAGATG 3'              SEQ ID NO:69

CAH interrogation oligo 23 (wild type) for mutation site 7

11642    5'GGGATCACAACGAGGAGAAG 3'              SEQ ID NO:70

CAH interrogation oligo 24 (pseudogene/mutant) for mutation site 7

EXAMPLE 14

Comparison of Thermophilic DNA Polymerases in a One-Step 70° C. Interrogation Reaction In this example, four different thermophilic DNA polymerases were used along with the thermophilic NDPK from Pfu in an interrogation reaction. The polymerases used were Taq (Promega, M166F), Pfu (*Pyrococcus furiosus* strain Vc1 DSM3638, Promega, M774A), Tvu (*Thermoactinomyces vulgaris*, purified at Promega), and Ath (*Anaeocellum thermophilum*, purified at Promega).

Cytomegalovirus (CMV) synthetic targets were generated by combining wild type oligonucleotide primers 9162 (SEQ ID NO:71) and 9165 (SEQ ID NO:72) or mutant oligonucleotide primers 9163 (SEQ ID NO:34) and 9166 (SEQ ID NO:33). The interrogation oligonucleotides used were wild type sequence 9211 (SEQ ID NO:7) and mutant sequence 9212 (SEQ ID NO:8).

Five nanograms of either the wild type or the mutant target (2.5 ng each of 9162 and 9165 for wild type or 9163 and 9166 for mutant) were combined with 1 µg of either the wild type probe, the mutant probe, or no probe, and water to a final volume of 20 µL. The solutions were heated for 5 minutes at 95° C. then cooled for 10 minutes at room temperature. Twenty microliters of 2× master mix were then added to each solution, and each was further incubated at 70° C. for 10 minutes. Four microliters of each solution were added to 100 µL of L/L Reagent (Promega F202A) and the relative light units (rlu) measured on a Turner® TD20/20 luminometer. The various combinations of target and probe assayed and their average resulting rlu values, corrected for background values, from duplicate solutions are listed below.

| 2 X Master Mix: | |
|---|---|
| 100 µL | 10 X Thermophilic DNA polymerase buffer (Promega, M190A) |
| 100 µL | 15 mM MgCl$_2$ (Promega, A351B) |
| 25 µL | 40 mM NaPPi (Promega, E350B) |
| 10 µL | 10 µM ADP (Sigma, A-5285) |

| 2 X Master Mix: | |
|---|---|
| 5 µL | Thermophilic polymerase (1 U enzyme/reaction) |
| 5 µl | Pfu NDPK (0.5 U/µL; 0.1 U/rxn) |
| 275 µL | water |

The Pfu NDPK was purified from a Pfu NDPK protein cloned into *E. coli* as described in Examples 15 and 16, below.

| Polymerase | Target | Probe | rlu | match:mismatch ratio |
|---|---|---|---|---|
| Taq | wild type | wild type | 129 | 128:1 |
|  | wild type | mutant | -2 |  |
|  | mutant | mutant | 62 | 95:1 |
|  | mutant | wild type | 0.65 |  |
| Pfu | wild type | wild type | 121 | 20:1 |
|  | wild type | mutant | 6 |  |
|  | mutant | mutant | 34 | 1:2 |
|  | mutant | wild type | 54 |  |
| Tvu | wild type | wild type | 898 | 89:1 |
|  | wild type | mutant | 10 |  |
|  | mutant | mutant | 1075 | 66:1 |
|  | mutant | wild type | 16 |  |
| Ath | wild type | wild type | 327 | 327:1 |
|  | wild type | mutant | 0 |  |
|  | mutant | mutant | 244 | 136:1 |
|  | mutant | wild type | 1.8 |  |

| | | |
|---|---|---|
| 9162 | 5' CGTGTATGCCACTTTGATATTACACCCATGAACGTG | SEQ ID NO:71 |
| | CTCATCGACGTCAACCCGCACAACGAGCT 3' | |
| 9165 | 5' CGTTGTGCGGGTTCACGTCGATGAGCACGTTCATGG | SEQ ID NO:72 |
| | GTGTAATATCAAAGTGGCATACACGAGCT 3' | |
| 9163 | 5'CGTGTATGCCACTTTGATATTACACCCGTGAACGTG | SEQ ID NO:34 |
| | CTCATCGACGTCAACCCGCACAACGAGCT 3' | |
| 9166 | 5'CGTTGTGCGGGTTCACGTCGATGAGCACGTTCACGG | SEQ ID NO:33 |
| | GTGTAATATCAAAGTGGCATACACGAGCT 3' | |
| 9211 | 5'CACTTTGATATTACACCCATG 3' (wild type primer) | SEQ ID NO:7 |
| 9212 | 5'CACTTTGATATTACACCCGTG 3' (mutant primer) | SEQ ID NO:8 |

EXAMPLE 15

Cloning and Expression of a Gene Encoding a NDPK Enzyme from Thermophilic Bacteria *Pyrococcus furiosis*

The cloning and expression of a gene from the thermophilic bacteria *Pyrococcus furiosis* [Pfu; Pfu-Vcl(DSM 3638)] is described in this Example. This gene encodes the nucleoside diphosphate kinase (NDPK) enzyme. The protein originates from a thermophile and remains active at elevated temperatures for a longer period of time than the corresponding protein from a mesophilic organism. The protein also remains active at room temperature longer than the corresponding mesophilic enzyme. If the protein were stable at elevated temperature, it could function in combination with a thermostable polymerase in a pyrophosphorylation reaction, thereby eliminating the need to carry out separate pyrophosphorylation and phosphate transfer steps as needed for the NDPK derived from yeast.

The amino acid sequences of known NDPKs (*Gene* 129:141–146, 1993 and the NCBI sequence of NDPK from *Pyrococcus horikoshii*) were compared and segments of high amino acid homology identified.

Two degenerate DNA primers were designed that would permit the DNA between them to be amplified. These primers, Pf1 (SEQ ID NO:75) and Pf2 (SEQ ID NO:76), are shown below, and were dissolved in TE buffer (10 mM Tris, 1 mM EDTA). A '6' in the primer sequence indicates an inosine that can hybridize to any base.

Chromosomal DNA from Pfu was isolated by resuspending frozen cell paste from a 3 mL overnight (about 18 hours) culture pellet in 1 mL TE buffer (10 mM Tris, 1 mM EDTA), lysing the cells by beating with zircon beads, followed by two phenol extractions and a chloroform extraction. The DNA in the supernatant was then ethanol precipitated, dried, and resuspended in TE buffer overnight (about 18 hours). The resuspended DNA was treated with 20 units of RNaseI, reprecipitated and resuspended in TE buffer.

The Pfu genomic DNA was used in the following DNA amplification reaction.

| | |
|---|---|
| 2 μL | 1.5 μg Pfu DNA (pre-denatured for 5 minutes at 99° C., then placed on ice) |
| 5 μL | PCR buffer |
| 4 μL | 25 mM MgCl$_2$ |

-continued

| | |
|---|---|
| 2 μL | each primer Pf1 and Pf2 (200 picomoles each) |
| 1 μL | 10 mM dNTP mix |
| 25 μL | water |
| 1 μL | Taq (5 units) |
| 10 μL | 5M betaine |

Different extension temperatures in the range from 41° C. to 55° C. were tested in the following PCR profile: 94° C., 2 minutes; (94° C., 15 or 40 seconds; 45° C. to 55° C., 45 or 90 seconds; 72° C., 1 or 2 minutes)×20; 72° C. 2 minutes. The profile varied for the different extension temperatures, with 41° C. and 43° C. extension temperatures having the lesser times, and the remaining extension temperatures having the longer times.

The reaction products were analyzed by gel electrophoresis on a 1.2% TBE agarose gel. The products of the reaction were detected by staining the gel with ethidium bromide and photographing the gel under UV light. A 300 bp DNA fragment was identified as the product of the reaction and was present to a greater extent when using extension temperatures from 41° C. to 47° C. The 300 bp fragment was gel purified (Promega, A7170) and cloned into pGEM-T vector (Promega, A3600).

The sequence of the insert was determined and found to encode an open reading frame. The translated amino acid sequence of this open reading frame matched the protein sequence of the *Pyrococcus horikoshii* NDPK gene with 94% homology.

A hybridization probe, Pf3 (SEQ ID NO:77), was designed from the sequence obtained. This probe was $^{32}$P labeled and used to identify the size of the DNA fragments encoding the corresponding gene in chromosomal digests of the DNA from Pfu using standard Southern blot hybridization methods.

A size-specific EcoR I library of DNA fragments from Pfu was produced by digesting Pfu chromosomal DNA with EcoR I, fractionating the DNA fragments using agarose gel electrophoresis, identifying the segment of the fractionated DNA that corresponded to the 2 Kb EcoR I fragment identified as containing the desired gene and isolating the DNA from the gel. The DNA isolated was cloned into plasmid pZERO2 (Invitrogen), and the resulting library was transformed into *E. coli* TOP10 (Invitrogen). The transformants were probed using the same probe employed during Southern hybridization and two clones were identified as potential candidate clones. From this analysis, an EcoR I fragment about 2 kb in size was identified as a target for additional cloning.

The sequences of the two candidate clones were found to contain the exact sequence present in the 300 bp DNA segments sequenced earlier in addition to DNA sequences loaded onto an SDS gel. After running, the gel was stained with Coomassie Blue.

After destaining in 1% acetic acid and 10% methanol, the lanes containing extracts from cells with the open reading frame were found to contain a large amount of a protein of about 14 Kd, the expected size of the gene product from the insert.

Then, a comparison of the open reading frame to the published sequence of the Pfu genome (University of Utah) was performed and the open reading frame was found to exactly match a region of the genome of this organism as expected.

```
Pf1   5' AT6AT6AA(AG)CC6GA(TC)G(GC)6GT 3'                         SEQ ID NO:75

Pf2   5' AA(AG)TC6CC6C(TG)6AT6GT6CC6GG 3'                         SEQ ID NO:76

Pf3   5' GAGAAGCACTATGAGGAGCAC 3'                                 SEQ ID NO:77

Pf4

5'ATGAACGAAGTTGAAAGAACATTGGTAATCATAAAGCCCGACGCAGTAGTT            SEQ ID NO:78

AGGGGTCTAATAGGTGAAATTATAAGCAGGTTTGAGAAGAAAGGCCTCAAGAT

TGTTGGAATGAAGATGATCTGGATAGACAGGGAGTTGGCTGAGAAGCACTATG

AGGAGCACAAAGGAAAGCCCTTCTTTGAGGCTCTCATAGATTACATAACGAAA

GCTCCAGTAGTTGTTATGGTGGTTGAGGGAAGGTATGCAGTAGAAGTAGTT

AGAAAGATGGCTGGAGCTACTGATCCAAAGGACGCAGCACCTGGGACAATTAG

GGGAGATTATGGACTTGACATAGGAGATGCAATCTACAACGTGATTCATGC

CAGTGATTCAAAGGAAAGTGCGGAGAGGGAAATAAGCCTGTACTTTAAACCTG

AAGAAATTTATGAATACTGCAAAGCTGCAGATTGGTTTTACAGGGAAAAGAAG

CAGGCTAAATGCTGA 3'

Pf5

MNEVERTLVIIKPDAVVRGLIGEIISRFEKKGLKIVGMKMIWIDRELAEKHYE            SEQ ID NO:79

EHKGKPFFEALIDYITKAPVVVMVVEGRYAVEVVRKMAGATDPKDAAPGTIRG

DYGLDIGDAIYNVIHASDSKESAEREISLYFKPEEIYEYCKAADWFYREKKQA

KC

Pf6   5' GGGTGCTTTTCATGAACGAAGTTGA 3'                              SEQ ID NO:80

Pf7   5' AAGGGCAAAAATTCTAGAGTTCAGCAT 3'                            SEQ ID NO:81
``` both 5' and 3' to that sequence. The open reading frame identified earlier was found to extend significantly beyond the limits of the 300 bp segment sequenced earlier. The additional segments of the open reading frame again showed good homology with NDPK. The Pfu NDPK nucleotide sequence is identified as Sequence Pf4 (SEQ ID NO:78) and the corresponding amino acid sequence is identified as Pf5 (SEQ ID NO:79). The protein codes for 161 amino acid residues.

The coding segments of the gene were amplified using primers Pf6 (SEQ ID NO:80) and Pf7 (SEQ ID NO:81), and placed into a high protein expression vector for *E. coli* JHEX25, an IPTG inducible promoter system (Promega). Bacterial transformants were grown in LB media and induced for protein expression. Samples of the induced bacterial cultures were boiled in 2×SDS Sample buffer and

EXAMPLE 16

Purification of Cloned Pfu NDPK Protein from *E. coli*

An initial fermentation of Top10 *E. coli* cells expressing the Pfu NDPK protein, as described in Example 24 yielded about 10 g of wet cell paste. The protein purification scheme was essentially that as described in Kim, S. et al. *Molecules and Cells*, 7:630, 1997. one gram of cell paste was resuspended in 10 mL of 20 mM Tris-acetate pH 7.4/1 mM EDTA/2 µg/mL aprotinin/0.1 mg/mL lysozyme and incubated at room temperature for 10 minutes. The suspension was then sonicated for 2 minutes at 50% cycle, held on ice for 5 minutes, then sonicated an additional 2 minutes. The suspension was centrifuged at 15,000×g for 20 minutes at 4° C. and the supernatant transferred to a new tube.

The supernatant was heated to 80° C. for 20 minutes to denature non-thermostable proteins. Precipitant was pelleted by centrifugation at 14,000×g for 20 minutes at 4° C. and supernatant was transferred to a new tube.

Ten milliliters of supernatant were applied to a 5 mL ATP-sepharose (Sigma, A-9264) affinity column equilibrated with Buffer A (20 mM Tris-acetate pH 7.4/20 mM NaCl/0.1 mM EDTA/3 mM MgCl$_2$/15 mM BME). The flow through was collected by gravity. The column was washed with 6 column volumes of Buffer B (Buffer A containing 500 mM NaCl). The bound protein was eluted in two steps: 5 mL Buffer B+1 mM dCTP (Promega, U122A) followed by 5 mL of Buffer B+1 mM ATP (Sigma, A-7699).

SDS-PAGE analysis of the purification fractions showed a large loss of total protein following the heat denaturation step, with the NDPK being the major band loaded on the column. About 50% of the loaded NDPK was in the flow-through fraction. Eluted NDPK appeared in both the dCTP and ATP elutions at greater than 80% purity.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed:

1. A method for enhancing the discrimination of analytical output in the determination of the presence or absence of a predetermined target nucleic acid sequence in a nucleic acid sample that comprises the steps of:
   (A) providing a plurality of separate treated samples, each sample containing (a) a nucleic acid that may contain said predetermined nucleic acid target sequence, said nucleic acid target sequence being hybridized when present with (b) a nucleic acid probe,
      a first probe of a first treated sample comprising (i) a 3'-terminal region sequence that is complementary to said nucleic acid target sequence and includes an identifier nucleotide that is complementary to a first predetermined nucleotide of said nucleic acid target sequence and (ii) a second sequence otherwise complementary to said nucleic acid target sequence except for a second predetermined nucleotide located 2 to about 10 nucleotides upstream from the 3'-terminus of said probe that is not complementary to a second nucleotide of said nucleic acid target sequence, and
      a second probe of a second treated sample comprising (i) a 3'-terminal sequence that is complementary to said nucleic acid target sequence except for an identifier nucleotide that is not complementary to said first-named predetermined nucleotide of said nucleic acid target sequence and (ii) a second sequence otherwise complementary to said nucleic acid target sequence except for said second predetermined nucleotide located 3 to about 10 nucleotides upstream from the 3'-terminus of said probe that is not complementary to a second predetermined nucleotide of said nucleic acid target sequence;
   (B) admixing each treated sample with a depolymerizing amount of an enzyme whose activity is to release one or more nucleotides from the 3'-terminus of a hybridized nucleic acid probe to form a treated reaction mixture, wherein said enzyme catalyzes pyrophosphorolysis;
   (C) maintaining the treated reaction mixtures for a time period sufficient to permit the enzyme to depolymerize hybridized nucleic acid probe and release an identifier nucleotide; and
   (D) analyzing the samples for the presence of released identifier nucleotide to obtain an analytical output, the ratio of the analytical output from the sample containing the first probe relative to that of the second probe being enhanced compared to the ratio of the analytical output from a similar sample containing a third probe of the same length having the same identifier nucleotide and total complementarity to said nucleic acid target sequence relative to that of a fourth probe of the same length whose identifier nucleotide is non-complementary to said first predetermined nucleotide and is otherwise totally complementary to said target nucleic acid sequence.

2. The method according to claim 1 wherein said identifier nucleotide is a nucleoside triphosphate.

3. The method according to claim 1 wherein said analytical output is obtained by luminescence spectroscopy.

4. The method according to claim 1 wherein said analytical output is obtained by fluorescence spectroscopy.

5. The method according to claim 1 wherein said analytical output is obtained by mass spectrometry.

6. The method according to claim 1 wherein said analytical output is obtained by absorbance spectroscopy.

7. The method according to claim 1 including the further steps of forming said first and second treated samples by
   (A) separately admixing a sample to be assayed with each of said first and second nucleic acid probes to form separate hybridization compositions, wherein the 3'-terminal region of said nucleic acid probes (a) hybridize with partial or total complementarity to said nucleic acid target sequence when that sequence is present in the sample and (b) include an identifier nucleotide;
   (B) maintaining said hybridization compositions for a time period sufficient to form treated samples that may contain said one predetermined nucleic acid target sequence hybridized with said nucleic acid probes.

8. The method according to claim 1 wherein said nucleic acid sample is obtained from a biological sample.

9. The method according to claim 2 wherein said nucleoside triphosphate is used to covert ADP to ATP using NDPK.

10. The method according to claim 9 wherein said NDPK is encoded by *Pyrococcus furiosis*.

11. The method of claim 1 wherein said enzyme whose activity is to release one or more nucleotides from the 3'-terminus of a hybridized nucleic acid probe is a thermostable DNA polymerase.

12. A method for decreasing background signal in an assay to detect the presence or absence of predetermined nucleic acid target sequence in a nucleic acid sample that comprises the steps of:
   (A) admixing a sample to be assayed with a pair of amplifying primers to form an extension composition in which said amplifying primers are hybridized to said nucleic acid target sequence when said target sequence is present, and wherein one of said pair of amplifying primers contains a 5'-terminus containing a plurality of nucleotide linkages resistant to cleavage by T7 gene 6 exonuclease or T3 gene 6 exonuclease or λ exonuclease;
   (B) reacting the extension composition with a polymerase and nucleotides to extend the amplifying primers to form nucleic acid strands when the predetermined nucleic acid target sequence is present in the extension composition and form a treated extension composition;
   (C) admixing said treated extension composition with T7 gene 6 exonuclease or T3 gene 6 exonuclease or λ exonuclease to form a strand removal composition;
   (D) maintaining the strand removal composition for a time period sufficient to substantially degrade hybridized nucleic acid strands not resistant to cleavage by T7 gene 6 exonuclease or T3 gene 6 exonuclease or λ exonuclease to form a treated sample;

(E) admixing said treated sample with a nucleic acid probe that hybridizes with said extended amplifying primer and includes an identifier nucleotide in the 3'-terminal region to form second hybrids;

(F) admixing the second hybrids with a depolymerizing amount of an enzyme whose activity is to release one or more nucleotides from the 3'-terminus of a hybridized nucleic acid probe to form a treated reaction mixture, wherein said enzyme catalyzes pyrophosphorolysis;

(G) maintaining the treated reaction mixture for a time period sufficient to permit the enzyme to depolymerize hybridized nucleic acid and release identifier nucleotides therefrom; and (H) analyzing for the presence of released identifier nucleotides to obtain an analytical output, the analytical output indicating the presence or absence of said nucleic acid target sequence.

13. The method according to claim 12 wherein the plurality of amplifying primer 5'-terminal linkages resistant to 5' to 3' exonuclease activity are phosphorothioate linkages.

14. The method according to claim 12 wherein the 5'-terminus of said amplifying primer contains two or three linkages resistant to the activity of said 5' to 3'-exonucleases.

15. The method according to claim 14 wherein the 5'-terminus of said amplifying primer contains two or three phosphorothioate linkages.

16. The method according to claim 12 wherein said identifier nucleotide is a nucleoside triphosphate.

17. The method according to claim 12 wherein said analytical output is obtained by luminescence spectroscopy.

18. The method according to claim 12 wherein said analytical output is obtained by fluorescence spectroscopy.

19. The method according to claim 12 wherein said analytical output is obtained by mass spectrometry.

20. The method according to claim 12 wherein said analytical output is obtained by absorbance spectroscopy.

21. The method according to claim 12 wherein said nucleic acid sample is obtained from a biological sample.

22. The method according to claim 16 wherein said nucleoside triphosphate is used to covert ADP to ATP using NDPK.

23. The method according to claim 22 wherein said NDPK is encoded by *Pyrococcus furiosis*.

24. The method of claim 12 wherein said enzyme whose activity is to release one or more nucleotides from the 3'-terminus of a hybridized nucleic acid probe is a thermostable polymerase.

25. The method of claim 12 wherein said a plurality of different primer pairs is admixed with said sample to be assayed, said primers being hybridized to a plurality of target nucleic acid sequences when those target sequences are present in said sample.

26. A process to determine the presence or absence of a predetermined single-stranded nucleic acid target sequence comprising the steps of:

(A) providing a depolymerization reaction mixture comprising (a) a pair of first and second complementary nucleic acid probes that form 3'-overhangs on both ends of the duplex formed when each of said pair of complementary nucleic acid probes is hybridized with the other, the first of said probes being complementary to the nucleic acid target sequence, (b) a hybrid between a third probe and the nucleic acid target sequence when the nucleic acid target sequence is present in the nucleic acid sample, and (c) a depolymerizing amount of an enzyme whose activity is to release nucleotides from the 3'-terminus of a hybridized nucleic acid wherein said enzyme catalyzes pyrophosphorolysis, wherein each of said first and third probes has an identifier nucleotide in its 3'-terminal region;

(B) maintaining the depolymerization reaction mixture for a time period sufficient to permit the enzyme to depolymerize the 3'-terminal region of said hybridized third probe to release identifier nucleotide and form a first treated reaction mixture;

(C) denaturing the products of the first treated reaction mixture to form a denatured treated reaction mixture;

(D) maintaining the denatured treated reaction mixture for a time period sufficient to form a second depolymerization reaction mixture that comprises (a) a hybrid formed between said first probe and said nucleic acid target sequence when the nucleic acid target sequence is present in the nucleic acid sample and (b) a hybrid formed between the 3'-terminal-depolymerized third probe and said second nucleic acid probe, one end of said hybrid having a blunt end or a 5'-overhang as well as an identifier nucleotide in the 3'-terminal region;

(E) depolymerizing hybrids (a) and (b) of step (D) to release identifier nucleotide from the 3'-terminal regions of said hybrids to form a second treated reaction mixture; and (F) analyzing said second treated reaction mixture for the presence of released identifier nucleotide to obtain an analytical output, the analytical output indicating the presence or absence of said nucleic acid target sequence.

27. The process according to claim 26 wherein said first and third probes are the same.

28. The method according to claim 26 wherein said identifier nucleotide is a nucleoside triphosphate.

29. The method according to claim 26 wherein said analytical output is obtained by luminescence spectroscopy.

30. The method according to claim 26 wherein said analytical output is obtained by fluorescence spectroscopy.

31. The method according to claim 26 wherein said analytical output is obtained by mass spectrometry.

32. The method according to claim 26 wherein said analytical output is obtained by absorbance spectroscopy.

33. The method according to claim 26 wherein said nucleic acid sample is obtained from a biological sample.

34. The method according to claim 28 wherein said nucleoside triphosphate is used to covert ADP to ATP using NDPK.

35. The method according to claim 34 wherein said NDPK is encoded by *Pyrococcus furiosis*.

36. The method of claim 26 wherein said enzyme whose activity is to release one or more nucleotides from the 3'-terminus of a hybridized nucleic acid probe is a thermostable polymerase.

37. A process to determine the presence or absence of a predetermined double-stranded nucleic acid target sequence comprising the following steps:

(A) providing a first reaction mixture comprising (a) first and second complementary nucleic acid probes that form 3'-overhangs on both ends of the duplex formed when each of said complementary nucleic acid probes is hybridized with the other, wherein said each of probes is complementary to one or the other strand of the nucleic acid target sequence and has an identifier nucleotide in its 3'-terminal region, (b) hybrids between a third and fourth probe and each of the two strands of the nucleic acid target sequence when the nucleic acid target sequence is present in the nucleic acid sample, said third and fourth probes each having an identifier nucleotide in its 3'-terminal region and (c) a depolymerizing amount of an enzyme whose activity is to release nucleotides from the 3'-terminus of a hybridized nucleic acid, wherein said enzyme catalyzes pyrophosphorolysis;

(B) maintaining the first reaction mixture for a time period sufficient to permit the enzyme to depolymerize hybridized nucleic acid to release identifier nucleotide from the 3'-terminal region of said hybridized third and fourth probes and form a treated first reaction mixture;

(C) denaturing the products of the treated first reaction mixture to form a denatured treated reaction mixture;

(D) maintaining the denatured treated reaction mixture for a time period sufficient to form a second reaction mixture that comprises a (a) hybrids that lack a 3'-overhang between each of the strands of the target nucleic acid and each of the first and second probes when the nucleic acid target sequence is present in the nucleic acid sample, and (b) hybrids between each of the first and seconds probes and 3'-terminal regiondepolymerized third and fourth probes, wherein each of said hybrids comprises one end that is blunt or has a 5'-overhang as well as an identifier nucleotide in the 3'-terminal region; and (E) depolymerizing the hybrids (a) and (b) of step (D) to release identifier nucleotide from the 3'-terminus of said hybridized probes to form a second treated reaction mixture; and (F) analyzing said second treated reaction mixture for the presence of released identifier nucleotide to obtain an analytical output, the analytical output indicating the presence or absence of said nucleic acid target sequence.

38. The process according to claim 37 wherein said first and third probes are the same.

39. The process according to claim 37 wherein steps A through D are repeated prior to conducting step E.

40. The method according to claim 37 wherein said identifier nucleotide is a nucleoside triphosphate.

41. The method according to claim 37 wherein said analytical output is obtained by luminescence spectroscopy.

42. The method according to claim 37 wherein said analytical output is obtained by fluorescence spectroscopy.

43. The method according to claim 37 wherein said analytical output is obtained by mass spectrometry.

44. The method according to claim 37 wherein said analytical output is obtained by absorbance spectroscopy.

45. The method according to claim 37 wherein said nucleic acid sample is obtained from a biological sample.

46. The method according to claim 40 wherein said nucleoside triphosphate is used o covert ADP to ATP using NDPK.

47. The method according to claim 46 wherein said NDPK is encoded by *Pyrococcus furiosis*.

48. The method of claim 37 wherein said enzyme whose activity is to release one or more nucleotides from the 3'-terminus of a hybridized nucleic acid probe is a thermostable polymerase.

* * * * *